US 12,193,332 B2

(12) United States Patent
Furuta et al.

(10) Patent No.: US 12,193,332 B2
(45) Date of Patent: Jan. 7, 2025

(54) METHOD OF MANUFACTURING PIEZOELECTRIC CERAMICS, PIEZOELECTRIC CERAMICS, PIEZOELECTRIC ELEMENT, ULTRASONIC MOTOR, OPTICAL APPARATUS, DUST REMOVING DEVICE, IMAGE PICKUP APPARATUS, ULTRASONIC PROBE, ULTRASONIC DIAGNOSTIC APPARATUS, AND ELECTRONIC APPARATUS

(71) Applicant: CANON KABUSHIKI KAISHA, Tokyo (JP)

(72) Inventors: Tatsuo Furuta, Tokyo (JP); Takanori Matsuda, Tokyo (JP); Hisato Yabuta, Tokyo (JP); Akira Uebayashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 816 days.

(21) Appl. No.: 17/222,120

(22) Filed: Apr. 5, 2021

(65) Prior Publication Data

US 2021/0328131 A1  Oct. 21, 2021

(30) Foreign Application Priority Data

Apr. 20, 2020  (JP) .................. 2020-074641

(51) Int. Cl.
*H01L 41/18* (2006.01)
*B06B 1/06* (2006.01)
(Continued)

(52) U.S. Cl.
CPC ......... *H10N 30/097* (2023.02); *B06B 1/0622* (2013.01); *B08B 7/028* (2013.01);
(Continued)

(58) Field of Classification Search
CPC .................................. H10N 30/8536
(Continued)

(56) References Cited

U.S. PATENT DOCUMENTS 4,675,123 A   6/1987 Tsunooka et al.
6,129,886 A   10/2000 Tachimoto et al.
(Continued)

FOREIGN PATENT DOCUMENTS

CN   104810471 A   7/2015
CN   106278257 A   1/2017
(Continued)

OTHER PUBLICATIONS

Notice of Reasons for Refusal in Japanese Application No. No. 2020-074641 (Nov. 2023).
(Continued)

*Primary Examiner* — Derek J Rosenau
(74) *Attorney, Agent, or Firm* — Venable LLP

(57) ABSTRACT

Provided are a piezoelectric ceramics which does not contain lead, has small temperature dependence of a piezoelectric constant within an operating temperature range, and has high density, a high mechanical quality factor, a satisfactory piezoelectric constant, and a small surface roughness, and a method of manufacturing the piezoelectric ceramics. The method of manufacturing a piezoelectric ceramics is characterized by including: sintering a compact containing a raw material at 1,000° C. or more to obtain a sintered compact; abrading the sintered compact; and annealing the abraded sintered compact at a temperature of 800° C. or more and less than 1,000° C.

17 Claims, 12 Drawing Sheets

(51) Int. Cl.
*B08B 7/02* (2006.01)
*C04B 35/468* (2006.01)
*C04B 35/645* (2006.01)
*H04N 23/81* (2023.01)
*H10N 30/097* (2023.01)
*H10N 30/853* (2023.01)
*G02B 7/14* (2021.01)

(52) U.S. Cl.
CPC ........ *C04B 35/4682* (2013.01); *C04B 35/645* (2013.01); *H04N 23/811* (2023.01); *H10N 30/8536* (2023.02); *C04B 2235/3208* (2013.01); *C04B 2235/3215* (2013.01); *C04B 2235/3263* (2013.01); *C04B 2235/3298* (2013.01); *C04B 2235/768* (2013.01); *G02B 7/14* (2013.01)

(58) Field of Classification Search
USPC ........................ 310/358; 252/62.9 R, 62.9 PZ
See application file for complete search history.

(56) References Cited

U.S. PATENT DOCUMENTS

| | | | |
|---|---|---|---|
| 7,906,889 B2 | 3/2011 | Furuta et al. | |
| 8,182,713 B2 | 5/2012 | Ren et al. | |
| 8,702,885 B2 | 4/2014 | Matsuda et al. | |
| 9,136,460 B2 | 9/2015 | Hayashi et al. | |
| 9,144,971 B2 | 9/2015 | Watanabe et al. | |
| 9,231,188 B2 | 1/2016 | Suzuki et al. | |
| 9,306,150 B2 | 4/2016 | Watanabe et al. | |
| 9,412,931 B2 | 8/2016 | Shimada et al. | |
| 9,614,141 B2 | 4/2017 | Shimizu et al. | |
| 9,722,170 B2 | 8/2017 | Watanabe et al. | |
| 9,806,251 B2 | 10/2017 | Kubota et al. | |
| 9,842,985 B2 | 12/2017 | Suzuki et al. | |
| 9,893,268 B2 | 2/2018 | Matsuda et al. | |
| 9,917,245 B2 | 3/2018 | Kubota et al. | |
| 10,424,722 B2 | 9/2019 | Matsuda et al. | |
| 10,727,395 B2 | 7/2020 | Yabuta et al. | |
| 10,868,232 B2 | 12/2020 | Saito et al. | |
| 11,201,279 B2 | 12/2021 | Watanabe et al. | |
| 2004/0214723 A1 | 10/2004 | Nonoyama et al. | |
| 2015/0171311 A1 | 6/2015 | Kubota et al. | |
| 2015/0214470 A1 | 7/2015 | Hayashi et al. | |
| 2015/0255703 A1* | 9/2015 | Furuta | B41J 2/14201 347/68 |
| 2016/0315245 A1* | 10/2016 | Kubota | B08B 7/02 |
| 2017/0101345 A1 | 4/2017 | Shimada et al. | |
| 2019/0044054 A1* | 2/2019 | Watanabe | C04B 35/4682 |
| 2021/0305492 A1 | 9/2021 | Ueda et al. | |

FOREIGN PATENT DOCUMENTS

| | | |
|---|---|---|
| JP | 1-206882 A | 8/1989 |
| JP | 10-279352 A | 10/1998 |
| JP | 2004-300019 A | 10/2004 |
| JP | 2009-215111 A | 9/2009 |
| JP | 2011-157252 A | 8/2011 |
| JP | 2012-503591 A | 2/2012 |
| JP | 2015-035587 A | 2/2015 |
| JP | 2015-164182 A | 9/2015 |
| JP | 2019-29671 A | 2/2019 |
| WO | 2010/036363 A2 | 4/2010 |

OTHER PUBLICATIONS

U.S. Appl. No. 17/345,259, filed Jun. 11, 2021, Ueda et al.
First Office Action in Chinese Application No. 202110413349.8 (Sep. 2022).
Decision of Rejection in Chinese Application No. 202110413349 (Sep. 2024).

* cited by examiner

METHOD OF MANUFACTURING PIEZOELECTRIC CERAMICS, PIEZOELECTRIC CERAMICS, PIEZOELECTRIC ELEMENT, ULTRASONIC MOTOR, OPTICAL APPARATUS, DUST REMOVING DEVICE, IMAGE PICKUP APPARATUS, ULTRASONIC PROBE, ULTRASONIC DIAGNOSTIC APPARATUS, AND ELECTRONIC APPARATUS

BACKGROUND OF THE INVENTION

Field of the Invention

The present disclosure relates to a piezoelectric ceramics and a method of manufacturing the piezoelectric ceramics. The present disclosure also relates to a piezoelectric element, an ultrasonic motor, an optical apparatus, a dust removing device, an image pickup apparatus, an ultrasonic probe, an ultrasonic diagnostic apparatus, and an electronic apparatus which use the piezoelectric ceramics.

Description of the Related Art

Lead zirconate titanate containing lead is a typical piezoelectric material, and is used in a variety of piezoelectric devices, such as an actuator, an oscillator, a sensor, and a filter. However, a lead content in a discarded piezoelectric material may elute into soil to adversely affect an ecosystem. Accordingly, in order to exclude lead from piezoelectric devices, research and development on lead-free piezoelectric materials are actively conducted.

When a piezoelectric element is used in a product, such as a household electrical appliance, it is required that the electromechanical coupling coefficient be large and the fluctuation thereof be small within an operating temperature range of the product. When the electromechanical coupling coefficient is small, the conversion efficiency from electric energy to mechanical energy is small, and the power consumption is increased. In addition, when the electromechanical coupling coefficient is greatly fluctuated (for example, by more than 35%) depending on the temperature, it becomes difficult to obtain stable element performance within the operating temperature range. The electromechanical coupling coefficient has a proportional relationship with a piezoelectric constant, and hence the fluctuation in electromechanical coupling coefficient also causes a fluctuation in piezoelectric constant. When the piezoelectric constant is fluctuated, distortion that varies depending on the temperature occurs even when a voltage is input in a constant manner. Accordingly, it is required to change a drive method for each temperature.

Further, regarding the fluctuation in electromechanical coupling coefficient, when a piezoelectric material undergoes a phase transition, the electromechanical coupling coefficient is increased as the temperature approaches a phase transition temperature. Accordingly, the phase transition of the piezoelectric material is the largest factor for fluctuating the electromechanical coupling coefficient. Thus, when changes in piezoelectric constant and electromechanical coupling coefficient within the operating temperature range of the product need to be reduced, a piezoelectric material that does not have a phase transition temperature within the operating temperature range is required.

Meanwhile, when the piezoelectric material is used in a resonance device, such as an ultrasonic motor, it is required that the mechanical quality factor indicating the sharpness of resonance be large. When the mechanical quality factor is small, the electric power required for operation becomes high, or the piezoelectric element generates heat to make drive control difficult. Accordingly, a piezoelectric material having a large mechanical quality factor is required.

In Japanese Patent Application Laid-Open No. 2009-215111, there is disclosed a lead-free piezoelectric material represented by the pseudo-binary solid solution of $\{[(Ba_{1-x1}M1_{x1})((Ti_{1-x}Zr_x)_{1-y1}N1_{y1})O_3]\text{-}\delta\%\ [((Ba_{1-y}Ca_y)_{1-x2}M2_{x2})(Ti_{1-y2}N2_{y2})O_3]\}$ (M1, N1, M2, and N2 each represent an additive element). $(Ba_{1-x1}M1_{x1})((Ti_{1-x}Zr_x)_{1-y1}N1_{y1})O_3$ is a rhombohedral crystal, and $((Ba_{1-y}Ca_y)_{1-x2}M2_{x2})(Ti_{1-y2}N2_{y2})O_3$ is a tetragonal crystal. A phase transition temperature between the rhombohedral crystal and the tetragonal crystal is adjusted to about room temperature by forming a solid solution of two components of different crystal systems. For example, there is a disclosure that $BaTi_{0.8}Zr_{0.2}O_3\text{-}50\%\ Ba_{0.7}Ca_{0.3}TiO_3$ had a phase transition temperature of about room temperature and a piezoelectric constant $d_{33}$ at 20° C. of 584 pC/N. Meanwhile, there is a disclosure that the material had a piezoelectric constant $d_{33}$ at 70° C. of 368 pC/N. That is, as a result of a temperature increase of 50° C., the piezoelectric constant $d_{33}$ was fluctuated by 37% as compared to the piezoelectric constant $d_{33}$ at 20° C. The electromechanical coupling coefficient has a proportional relationship with the piezoelectric constant, and hence it is conceived that the electromechanical coupling coefficient is also fluctuated to the same degree.

In the piezoelectric material of Japanese Patent Application Laid-Open No. 2009-215111, the phase transition in which the piezoelectric characteristics are maximized occurs in the vicinity of room temperature. Thus, although the piezoelectric material exhibits a high piezoelectric constant in the vicinity of room temperature, there is a problem in that the piezoelectric constant and the electromechanical coupling coefficient are significantly fluctuated when the temperature is changed. In addition, the inventors of the present disclosure have made extensive investigations, and as a result, have found that there is a problem in that the mechanical quality factor at room temperature is as low as less than 500.

Meanwhile, in Japanese Patent Application Laid-Open No. 2015-035587, there is described a method involving abrading a piezoelectric material, and then subjecting the piezoelectric material to heat treatment at a temperature of 1,000° C. or more to alleviate residual stress generated during the abrasion, to thereby improve the piezoelectric characteristics. However, as a result of the extensive investigations made by the inventors of the present disclosure, the following was found. Although a high piezoelectric constant and a high electromechanical coupling coefficient are obtained, the surface of the piezoelectric material may undergo grain growth to become rough when the piezoelectric material is subjected to heat treatment at a temperature of 1,000° C. or more. In the case where the surface becomes rough, when a vibrating body that vibrates together with the piezoelectric material is bonded to the surface thereof with an adhesive, the adhesive enters recesses on the rough surface, with the result that the adhesive becomes thick, and vibration is not easily transmitted from the piezoelectric material to the vibrating body. As a result, there is a problem in that the drive efficiency deteriorates, and the power consumption is increased. In addition, in the case where the surface of the piezoelectric material is rough, when an electrode is arranged on the surface of the piezoelectric material, the electrode enters the recesses of the rough surface, and the thickness of the electrode is increased to suppress the vibration of the piezoelectric material. Also in this case, there is a problem in that the drive efficiency deteriorates, and the power consumption is increased.

In the related art, there is a problem in that the piezoelectric performance of a lead-free piezoelectric material is greatly fluctuated within the operating temperature range of the piezoelectric material, the mechanical quality factor is small, and the surface becomes rough even when an attempt is made to improve the piezoelectric performance by heat treatment at 1,000° C. or more.

The present disclosure has been made to solve the above-mentioned problems, and provides a piezoelectric ceramics which does not contain lead, has small temperature dependence of a piezoelectric constant within an operating temperature range, and has a high density, a high mechanical quality factor, a satisfactory piezoelectric constant, and a small surface roughness, or a method of manufacturing the piezoelectric ceramics.

In addition, the present disclosure provides a piezoelectric element, an ultrasonic motor, an optical apparatus, a dust removing device, an image pickup apparatus, an ultrasonic probe, an ultrasonic diagnostic apparatus, and an electronic apparatus which use the piezoelectric ceramics.

SUMMARY OF THE INVENTION

A method of manufacturing a piezoelectric ceramics of the present disclosure for solving the above-mentioned problems is characterized by including: sintering a compact containing a raw material at 1,000° C. or more to obtain a sintered compact; abrading the sintered compact; and annealing the abraded sintered compact to at 800° C. or more and less than 1,000° C.

A method of manufacturing a piezoelectric element of the present disclosure is characterized in that arranging an electrode on the piezoelectric ceramics is performed before the annealing, and the electrode is baked by the annealing.

A piezoelectric ceramics of the present disclosure is a piezoelectric ceramics including titanium and barium as main components, and is characterized in that the piezoelectric ceramics has an electromechanical coupling coefficient $k_{31}$ at room temperature of 0.252 or more, and wherein the piezoelectric ceramics has a roughness Ra of 0.19 µm or less on at least a part of a surface thereof.

A piezoelectric element of the present disclosure is characterized by including an electrode and a piezoelectric ceramics.

An ultrasonic motor of the present disclosure is characterized by including at least a vibrating body in which the piezoelectric element or laminated piezoelectric element is arranged and a movable body configured to be brought into contact with the vibrating body.

An optical apparatus of the present disclosure is characterized by including the ultrasonic motor provided to a drive unit.

A vibration device of the present disclosure is characterized by including a vibrating body in which the piezoelectric element is arranged on a vibrating plate.

A dust removing device of the present disclosure is characterized by including the vibration device provided to a vibrating portion.

An image pickup apparatus of the present disclosure is an image pickup apparatus including at least the dust removing device and an image pickup element unit, and is characterized in that a vibrating plate of the dust removing device is arranged on a light receiving surface side of the image pickup element unit.

An ultrasonic probe of the present disclosure is characterized by including the piezoelectric element, in which the piezoelectric element is configured to transmit and receive a signal.

An ultrasonic diagnostic apparatus of the present disclosure is characterized by including at least the ultrasonic probe and an image output portion.

An electronic apparatus of the present disclosure is characterized by including a piezoelectric acoustic component including the piezoelectric element.

Further features of the present disclosure will become apparent from the following description of exemplary embodiments with reference to the attached drawings.

DESCRIPTION OF THE EMBODIMENTS

Figure 1:
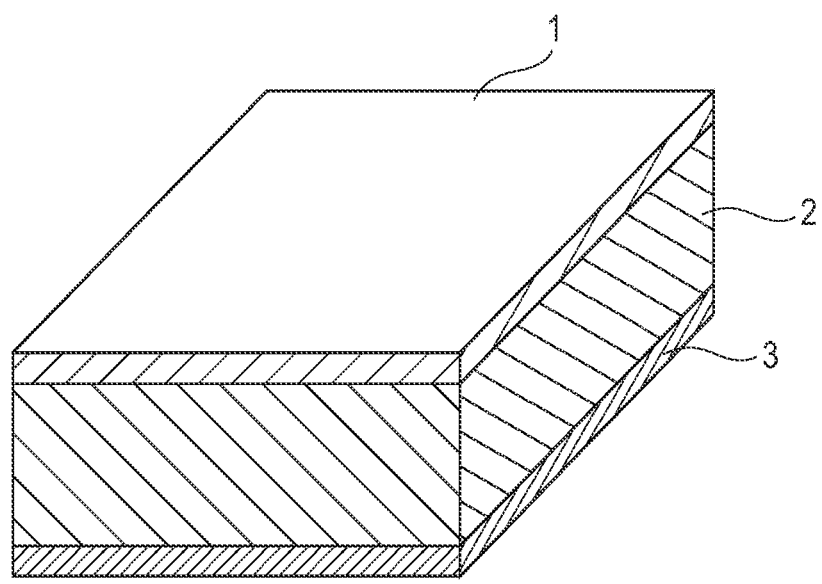
FIG. 1 is a schematic view for illustrating a configuration of a piezoelectric element according to one embodiment of the present disclosure.

Now, embodiments of the present disclosure are described with reference to the drawings. The present disclosure is not limited to the following description, and various configurations may be adopted as long as the spirit of the present disclosure is satisfied.

The present disclosure provides a lead-free piezoelectric ceramics which has a high mechanical quality factor, has small temperature dependence of an electromechanical coupling coefficient within an operating temperature range (for example, within a range of 0° C. or more and 60° C. or less), and has a high density, a high electromechanical coupling coefficient, and a small surface roughness, and a method of manufacturing the piezoelectric ceramics. The piezoelectric ceramics of the present disclosure may be used for various applications, such as a memory and a sensor, through use of the characteristics as a ferroelectric.

A method of manufacturing a piezoelectric ceramics of the present disclosure includes: sintering a compact containing a raw material at 1,000° C. or more to obtain a sintered compact; abrading the sintered compact; and annealing the abraded sintered compact at 800° C. or more and less than 1,000° C.

Now, a specific method of manufacturing a piezoelectric ceramics of the present disclosure is described.

(Raw Material Powder)

A raw material to be used in the method of manufacturing a piezoelectric ceramics of the present disclosure is solid powder of, for example, an oxide, a carbonate, a nitrate, or an oxalate, containing constituent elements forming the piezoelectric ceramics, or mixed powder thereof.

It is more preferred that the content of lead (Pb) in the raw material be less than 1,000 ppm because the burden on the environmental is small.

Preferred examples of the elements forming the raw material include Li, Na, Mg, Al, Si, K, Ca, Sc, Ti, V, Cr, Mn, Fe, Co, Zn, Ge, Sr, Y, Zr, Nb, Mo, Sn, Sb, Ba, Hf, Ta, Bi, La, Nd, Sm, Eu, Gd, Tb, Dy, Ho, Er, and Yb.

The raw material may be subjected to heat treatment in order to be homogenized, or may be crushed after the heat treatment. It is preferred that the heat treatment for homogenizing the raw material be performed within a range of 800° C. or more and 1,300° C. or less because the raw material is easily crushed after the heat treatment.

(Granulation)

The raw material to be used in the method of manufacturing a piezoelectric ceramics of the present disclosure may be granulated, and a granulation method therefor is not particularly limited. Examples of binders that may be used for granulation include polyvinyl alcohol (PVA), polyvinyl butyral (PVB), and an acrylic resin. The amount of the binder added to the mixed powder is preferably from 1 part by weight to 10 parts by weight, more preferably from 2 parts by weight to 5 parts by weight from the viewpoint that the density of a compact is increased. The most preferred granulation method is a spray drying method from the viewpoint that the particle diameter of granulated powder can be made more uniform.

(Compact)

A compact to be used in the method of manufacturing a piezoelectric ceramics of the present disclosure is a compact obtained by solidifying the raw material powder into a desired shape, and a production method therefor is not particularly limited. The compact is a solid product produced from raw material powder, granulated powder (binder), or a slurry. As a method of producing the compact, uniaxial pressing, cold hydrostatic pressing, warm hydrostatic pressing, cast molding and extrusion, or the like may be used. In addition, the raw material in a slurry state may be formed into a sheet through use of a doctor blade method and dried, or the sheets may be stacked and molded into a target shape.

(Calcination)

A sintering method in the method of manufacturing a piezoelectric ceramics of the present disclosure includes the step of sintering a compact containing the above-mentioned raw material at 1,000° C. or more to obtain a sintered compact. As the sintering method, there are given sintering using an electric furnace, sintering using a gas furnace, an energization heating method, a microwave sintering method, a millimeter-wave sintering method, hot isostatic pressing (HIP), and the like. The sintering using an electric furnace or a gas furnace may be performed in a continuous furnace or a batch furnace.

When the compact is sintered at 1,000° C. or more, each compound contained in the raw material reacts to grow crystals sufficiently. Examples of the sintered compact obtained by calcination include a sintered compact containing titanium and barium as main components, a sintered compact containing one or more kinds selected from lithium, potassium, and sodium, and niobium as main components, a sintered compact containing bismuth and titanium as main components, a sintered compact containing bismuth, iron, and cobalt as main components, a sintered compact containing bismuth, titanium, and sodium as main components, and a sintered compact containing a combination of the foregoing as main components.

In the case of a raw material containing barium titanate as a main component, the sintering temperature is preferably 1,100° C. or more and 1,550° C. or less, more preferably 1,100° C. or more and 1,380° C. or less from the viewpoint of setting the particle diameter of a sintered compact within a range of from 3 µm to 30 µm. There is an advantage in that a piezoelectric ceramics obtained from a sintered compact sintered within the above-mentioned temperature ranges has a high density.

Further, in order to stabilize the characteristics of the piezoelectric ceramics obtained by the sintering treatment with good reproducibility, it is preferred that the sintering treatment be performed at a constant sintering temperature within the above-mentioned ranges for 2 hours or more and 24 hours or less.

(Abrasion)

The method of manufacturing a piezoelectric ceramics of the present disclosure includes the step of abrading a sintered compact obtained by the sintering as described above. Herein, the abrasion refers to the step of scraping a part or an entirety of a surface of the sintered compact and adjusting the abraded surface to an arbitrary roughness.

The roughness refers to a roughness Ra which is an arithmetic average roughness, and is obtained by expressing an average value of distances from a reference line in a section in terms of micrometers (µm) with an average value of irregularities of the surface being as the reference line. As a method of measuring the surface roughness, based on the Japanese Industrial Standards (JIS B0601:2013), a measurement distance L is divided by "n" through use of a stylus type surface profilometer, and the i-th height is represented by "$y_i$". Thus, the roughness Ra can be obtained by the following expression (1). It is preferred that a distal end portion of a stylus be as small as possible, and it is preferred to use, for example, a stylus having a radius of curvature of a distal end portion of 1 μm.

$$Ra = \frac{1}{n}\sum_{i=1}^{n}|y_i| \quad (1)$$

Before and after the step of abrading the sintered compact, the step of deburring by barrel abrasion, blast abrasion, or the like, and the step of processing to a desired size through use of a lathe, a grinder, or a cutting machine may be included.

The abrading step includes mechanical abrasion, chemical abrasion, and CMP abrasion, and it is only required that those steps be combined to obtain a desired surface roughness.

The mechanical abrasion refers to abrasion to be performed through use of a machine. When the mechanical abrasion is performed, it is only required to use a machine selected from an abrasive machine, a lapping machine, a polishing machine, and a buff abrasive machine. As long as the surface roughness can be adjusted, for example, the step of using a precision grinder using an extremely fine grinding stone or the like may be adopted as the abrading step.

The chemical abrasion refers to an abrasion method involving immersing a metal in an abrasion solution, and corroding the surface of the metal by a chemical reaction through the action of an acid or an alkali. For example, there is a rotary type method involving attaching an abrasion pad on a disc-shaped surface plate, dropping a liquid abrasive containing chemical components and fine particles onto the abrasion pad, and performing abrasion while rotating the abrasion pad.

The CMP abrasion refers to a procedure obtained by combining the mechanical abrasion and the chemical abrasion, which is a method involving causing a chemical action between abrasive grains and a metal and between an abrasive liquid and a grinding liquid, as well as a mechanical action in which the surface of the metal is scraped with the abrasive grains, and flattening the surface through the physical abrasion and the chemical reaction.

In order to omit the abrading step, the sintered compact may also be molded into a desired shape after the sintering, but the surface of the sintered compact immediately after the sintering undergoes growth of crystal grains, and hence the surface roughness is enlarged. Accordingly, the abrading step is required in order to obtain a desired roughness Ra (for example, a roughness Ra of 0.19 μm or less) on at least a part of the surface.

(Annealing)

The method of manufacturing a piezoelectric ceramics of the present disclosure includes the step of annealing the abraded sintered compact at 800° C. or more and less than 1,000° C.

It is conceived that crystal defects occur on the surface of the sintered compact that has undergone the above-mentioned abrading step. Accordingly, the crystal defects are repaired, and the electromechanical coupling coefficient of the piezoelectric ceramics is improved by performing the annealing at 800° C. or more and less than 1,000° C. When the annealing is performed at 1,000° C. or more, the crystal grains grow to increase in size. As a result, even when the surface roughness Ra is adjusted in the abrading step described above, the surface roughness Ra is increased by the annealing. With this, the surface roughness Ra of each of the non-abraded surface and the abraded surface is increased, and hence the thickness is increased irrespective of which surface an adhesive or an electrode is applied to, with the result that the vibration efficiency of the piezoelectric ceramics deteriorates. In addition, when the temperature at which the annealing is performed is less than 800° C., a satisfactory electromechanical coupling coefficient is not obtained.

The temperature at which the annealing is performed is preferably 900° C. or more and less than 1,000° C., more preferably 950° C. or more and less than 1,000° C., because the crystal defects on the abraded surface are further repaired, and the electromechanical coupling coefficient is further improved.

The method of performing the annealing is not particularly limited. It is only required that sintering using an electric furnace, sintering using a gas furnace, an energization heating method, a microwave sintering method, a millimeter-wave sintering method, hot isostatic pressing (HIP), or the like be used in the same manner as in the method of obtaining a sintered compact by sintering, and a continuous furnace or a batch furnace may be used.

It is preferred that the annealing be performed in an air atmosphere because the crystal defects are easily repaired.

In the method of manufacturing a piezoelectric ceramics of the present disclosure, it is preferred that the time for keeping the temperature be 6 minutes or more and less than 10 hours in the annealing step.

In the annealing, it is preferred that the time for keeping the temperature be 6 minutes or more and less than 10 hours, because crystal grain defects are repaired, and the electromechanical coupling coefficient is improved. It is more preferred that the time for keeping the temperature be 2 hours or more and less than 5 hours, because the crystal defects are efficiently and sufficiently repaired, and the electromechanical coupling coefficient is further improved.

Next, a specific method of manufacturing a piezoelectric element of the present disclosure is described.

A material for an electrode to be used is not particularly limited as long as the material can be baked within a temperature range of 800° C. or more and less than 1,000° C., and may be any material usually used for a piezoelectric element. Examples thereof may include metals, such as Ti, Pt, Ta, Ir, Au, Fe, Cr, Ni, Pd, Ag, Cu, Sn, In, Sr, and Al, and compounds thereof. An electrode paste containing water, an organic substance, and the like in the electrode material is applied to an abraded sintered compact, and then the electrode paste is baked by annealing. Herein, when Sn, In, Sr, Al, or the like is selected as the electrode material for baking by the annealing, the melting point thereof is low, and hence it is required to raise the melting point, for example, by mixing the electrode material with another metal. In addition, it is preferred that baking by the annealing be performed in an air atmosphere. However, when Al, Fe, Ni, Cu, or the like is selected as the electrode material, the electrode material is liable to be oxidized, and hence it is preferred that the annealing be performed in a nitrogen atmosphere or the like. With this, the crystal defects on the abraded surface of the sintered compact are repaired by the annealing to improve the electromechanical coupling coefficient, and simultaneously, the electrode is also baked, with the result that the number of steps for manufacturing the piezoelectric element is reduced, and a manufacturing cost can be reduced. As a general electrode material that can be baked within a temperature range of 800° C. or more and less than 1,000° C., there is given Ag. For example, in the case of a Ag electrode, the melting point may be adjusted by mixing Pd with the electrode material, as required. The thickness of the electrode is preferably from 5 nm to 10 more preferably 5 μm or less because the vibration of the piezoelectric element is not inhibited.

The electrode may be baked after the annealing step. In this case, the annealing step is performed substantially twice, but the effect of improving the electromechanical coupling coefficient is similarly obtained. A method of forming an electrode when forming the electrode after the annealing step is not particularly limited, and it is only required that the electrode be formed by a sputtering method, a vapor deposition method, a plating method, or the like.

It is preferred that the piezoelectric ceramics to be used in the method of manufacturing a piezoelectric element of the present disclosure contain titanium and barium as main components. Barium titanate that is a compound of titanium and barium is widely used in capacitors, and raw materials thereof have low cost with less variation in quality. Accordingly, it is preferred that the piezoelectric ceramics contain titanium and barium as main components.

The piezoelectric ceramics of the present disclosure contains titanium and barium as main components, has an electromechanical coupling coefficient $k_{31}$ at room temperature of 0.252 or more, and has a roughness Ra of 0.19 μm or less on at least a part of a surface thereof.

The piezoelectric ceramics of the present disclosure contains titanium and barium as main components. The piezoelectric ceramics containing titanium and barium as main components has a high electromechanical coupling coefficient, and hence such piezoelectric ceramics is preferred because the power consumption for vibrating the piezoelectric ceramics is decreased. In addition, such piezoelectric ceramics is preferred, because the piezoelectric ceramics has a high piezoelectric constant "$d_{31}$" according to the following expression (2), and the vibration of a piezoelectric element becomes large.

$$d_{31} = k_{31}\sqrt{\frac{\varepsilon_{33}}{Y_{11}}} \qquad (2)$$

When "$k_{31}$" is 0.252 or more, the power consumption at the time of drive is decreased. Further, it is more preferred that the "$k_{31}$" be 0.270 or more because a sufficient vibration displacement amount is obtained even when the voltage at the time of drive is lowered, with the result that a loss on a drive circuit generated depending on the magnitude of the drive voltage is reduced, and the power consumption is further decreased.

The piezoelectric ceramics of the present disclosure has a surface roughness Ra of 0.19 μm or less on at least a part of the surface.

In the case where the piezoelectric ceramics has a surface roughness Ra of more than 0.19 μm, when a vibrating body or the like that vibrates together with the piezoelectric ceramics is bonded to the surface thereof with an adhesive, the adhesive enters recesses on the rough surface, with the result that the adhesive becomes thick, and vibration is not easily transmitted from the piezoelectric ceramics to the vibrating body. Further, in the case where the surface of the piezoelectric ceramics is rough, when an electrode is provided on the surface of the piezoelectric ceramics, the thickness of the electrode is increased for the same reason as that of the adhesive to suppress the vibration of the piezoelectric ceramics, with the result that the drive efficiency deteriorates.

It is preferred that the surface roughness Ra be 0.15 μm or less because the irregularities of the electrode are small, with the result that the distribution of a voltage applied to the piezoelectric ceramics becomes uniform, and a larger electromechanical coupling coefficient is obtained. It is more preferred that the surface roughness Ra be 0.10 μm or less because a further larger electromechanical coupling coefficient is obtained.

It is preferred that the piezoelectric ceramics of the present disclosure contain an oxide containing Ba, Ca, Ti, and Zr, and Mn, the molar ratio "x" of the Ca with respect to the sum of the Ba and the Ca be 0.02≤x≤0.30, the molar ratio "y" of the Zr with respect to the sum of the Ti and the Zr be 0.020≤y≤0.095, the molar ratio "y" and the molar ratio "x" have a relationship of y≤x, the molar ratio "a" of the sum of the Ba and the Ca with respect to the sum of the Ti and the Zr be 1.00≤a≤1.01, and the content of the Mn with respect to 100 parts by weight of the oxide be 0.02 part by weight or more and 0.40 part by weight or less in terms of a metal.

It is preferred that the piezoelectric ceramics of the present disclosure contain an oxide containing Ba, Ca, Ti, and Zr, and Mn.

The raw material for manufacturing the piezoelectric ceramics of the present disclosure is formed of, for example, a metal compound, such as a Ba compound, a Ca compound, a Ti compound, a Zr compound, or a Mn compound.

Examples of the Ba compound that may be used include barium oxide, barium carbonate, barium oxalate, barium acetate, barium nitrate, barium titanate, barium zirconate, and barium zirconate titanate.

Examples of the Ca compound that may be used include calcium oxide, calcium carbonate, calcium oxalate, calcium acetate, calcium titanate, and calcium zirconate.

Examples of the Ti compound that may be used include titanium oxide, barium titanate, barium zirconate titanate, and calcium titanate.

Examples of the Zr compound that may be used include zirconium oxide, barium zirconate, barium zirconate titanate, and calcium zirconate.

Examples of the Mn compound that may be used include manganese carbonate, manganese monoxide, manganese dioxide, trimanganese tetraoxide, and manganese acetate.

Herein, the content of Mn "in terms of a metal" indicates the following. The contents of respective metals of Ba, Ca, Ti, Zr, and Mn are measured from the piezoelectric ceramics by X-ray fluorescence (XRF) analysis, inductively coupled plasma (ICP) emission spectrochemical analysis, atomic absorption analysis, or the like. From the contents, elements forming a metal oxide represented by the following general formula (3) is converted into an oxide, and the content of Mn is indicated by a value obtained based on a ratio of the Mn weight with respect to the total weight of the elements of 100.

$(Ba_{1-x}Ca_x)_a(Ti_{1-y}Zr_y)O_3$ \hfill (3)

It is preferred that the piezoelectric ceramics of the present disclosure contain a perovskite-type metal oxide as a main phase from the viewpoint of an insulation property. The perovskite-type metal oxide refers to a metal oxide having a perovskite-type structure (sometimes referred to as "perovskite structure") as described in the 5th edition of the Iwanami Physical and Chemical Dictionary (Iwanami Shoten, Publishers, published on Feb. 20, 1998). A metal oxide having a perovskite-type structure is represented by the chemical formula of $ABO_3$ as in the general formula (3). In the perovskite-type metal oxide, the elements A and B occupy specific positions in a unit cell called an A site and a B site, respectively, in the form of ions. For example, in the case of a cubic unit cell, the element A is located at an apex of a cube, and the element B is located at a body center. The element O occupies a face-centered position of the cube as an anion of oxygen.

Whether or not the perovskite-type metal oxide is a main phase is determined by, for example, whether the maximum diffraction intensity derived from the perovskite-type metal oxide is 100 times or more the maximum diffraction intensity derived from an impurity phase in X-ray diffraction. It is preferred that the piezoelectric ceramics be formed of only the perovskite-type metal oxide because the insulation property becomes highest. The "main phase" refers to a case in which, when the powder X-ray diffraction of the piezoelectric ceramics is performed, the strongest diffraction intensity peak is ascribed to the perovskite-type structure. It is more preferred that the piezoelectric ceramics contain a perovskite-type metal oxide as a "single phase" in which crystals each having a perovskite-type structure occupy substantially the entire piezoelectric ceramics.

The metal oxide represented by the general formula (3) means that the metal elements located at the A site are Ba and Ca, and the metal elements located at the B site are Ti and Zr. However, a part of Ba and Ca may be located at the B site. Similarly, a part of Ti and Zr may be located at the A site.

In the general formula (3), the molar ratio of the elements at the site B to the element O is 1:3, but the ratio of the element amounts may be slightly different (for example, from 1.00:2.94 to 1.00:3.06).

In the piezoelectric ceramics of the present disclosure, it is preferred that the range of "x" be $0.02 \leq x \leq 0.30$, the range of "y" be $0.020 \leq y \leq 0.095$, and the "y" and the "x" satisfy a relationship of $y \leq x$. In addition, it is preferred that "a", which is a molar ratio of a sum of the Ba and the Ca to a sum of the Ti and the Zr, be $1.00 \leq a \leq 1.01$ because a satisfactory electromechanical coupling coefficient is obtained within the operating temperature range.

It is preferred that the range of the "x" of the piezoelectric ceramics of the present disclosure be $0.02 \leq x \leq 0.30$. When the "x" is less than 0.02, the phase transition temperature (hereinafter referred to as "$T_{ot}$") from an orthorhombic crystal to a tetragonal crystal becomes higher than 0° C., with the result that the temperature dependence of an electromechanical coupling coefficient and a piezoelectric constant within the operating temperature range is increased. The electromechanical coupling coefficient becomes maximum in the vicinity of the phase transition temperature, which indicates a local maximum value or an inflection point. Accordingly, when the phase transition is present within the operating temperature range of a device, the performance of the device extremely varies depending on the temperature, and the control of the device may become difficult. Accordingly, it is preferred that the phase transition, which is the largest factor for fluctuating the electromechanical coupling coefficient, be not within the operating temperature range. It is preferred that the phase transition temperature be far away from the operating temperature range because the temperature dependence of the electromechanical coupling coefficient within the operating temperature range is lowered.

Meanwhile, when the "x" is more than 0.30, Ca is not easily formed into a solid solution, and $CaTiO_3$ that is an impurity phase is generated, with the result that the electromechanical coupling coefficient and the piezoelectric constant are decreased. In addition, from the viewpoint of obtaining a more preferred electromechanical coupling coefficient and a more preferred piezoelectric constant, $x \leq 0.26$ is preferred, $x \leq 0.17$ is more preferred.

It is preferred that the range of the "y" of the piezoelectric ceramics of the present disclosure be $0.020 \leq y \leq 0.095$. When the "y" is 0.020 or more, the dielectric constant at room temperature can be increased to further improve the electromechanical coupling coefficient. Further, when the Zr amount "y" is more than 0.020, a satisfactory electromechanical coupling coefficient and a satisfactory piezoelectric constant are obtained. Accordingly, the range of "y" is preferably $y \geq 0.020$. From the viewpoint of obtaining a more preferred electromechanical coupling coefficient, the range of the "y" is $y \geq 0.050$. It is not preferred that the "y" be more than 0.095 because the Curie temperature (hereinafter referred to as "Tc") may be less than 100° C. In order to obtain a satisfactory electromechanical coupling coefficient and a satisfactory piezoelectric constant and set the Tc to 100° C. or more, it is more preferred that the range of the "y" be $0.020 \leq y \leq 0.095$.

It is preferred that the range of the "a", which is the molar ratio $\{a=(Ba+Ca)/(Zr+Ti)\}$ of the sum of the Ba and the Ca to the sum of the Ti and the Zr, be $1.00 \leq a \leq 1.01$. When the "a" is less than 1.00, abnormal grain growth occurs at the time of sintering. Furthermore, the average particle diameter becomes more than 50 μm, and the mechanical strength of the material is decreased. When the "a" is more than 1.01, a high-density piezoelectric ceramics is not obtained. When the density of the piezoelectric ceramics is low, the electromechanical coupling coefficient is decreased.

In the present disclosure, the density of an insufficiently calcined sample is smaller by 5% or more than that of a sufficiently calcined high-density sample. In order to obtain a piezoelectric ceramics having high density and high mechanical strength, the range of the "a" is preferably $1.00 \leq a \leq 1.01$.

It is preferred that the piezoelectric ceramics of the present disclosure contain Mn in an amount of 0.02 part by weight or more and 0.40 part by weight or less in terms of a metal with respect to 100 parts by weight of the perovskite-type metal oxide represented by the general formula (3). When the Mn within the above-mentioned ranges is contained, the mechanical quality factor is increased. However, when the content of the Mn is less than 0.02 part by weight, the effect of increasing the mechanical quality factor is not obtained. Meanwhile, when the content of the Mn is more than 0.40 part by weight, the insulation resistance of the piezoelectric ceramics is decreased. When the insulation resistance is low, the dielectric loss tangent at room temperature measured by applying an AC electric field having a frequency of 1 kHz and an electric field intensity of 10 V/cm through use of an impedance analyzer exceeds 0.01. Alternatively, the resistivity becomes 1 GΩcm or less.

The Mn is not limited to metal Mn. It is only required that the Mn be contained in the piezoelectric ceramics as a Mn component, and the form of being contained thereof is not limited. For example, the Mn may be formed into a solid solution at the B site or may be contained in a grain boundary. Alternatively, the Mn component may be contained in the piezoelectric ceramics in the form of a metal, an ion, an oxide, a metal salt, a complex, or the like. More preferably, the Mn is present from the viewpoints of an insulation property and ease of sintering.

It is preferred that the piezoelectric ceramics of the present disclosure have a mechanical quality factor Qm of 1,000 or more.

When the mechanical quality factor of the piezoelectric ceramics is 1,000 or more, the electric power required for drive is low, and the heat generation of the piezoelectric ceramics can be suppressed.

It is preferred that the piezoelectric ceramics of the present disclosure contain Bi in an amount of 0.042 part by weight or more and 0.850 part by weight or less in terms of a metal with respect to 100 parts by weight of the perovskite-type metal oxide represented by the general formula (3). When the content of the Bi is less than 0.042 part by weight, the effect of decreasing the phase transition temperature and improving the mechanical quality factor is not obtained. When the content of the Bi is more than 0.850 part by weight, the electromechanical coupling coefficient is decreased by more than 30% as compared to the case in which the Bi is not contained.

In the piezoelectric ceramics of the present disclosure, the Bi may be in a grain boundary or may be formed into a solid solution in the perovskite-type structure of (Ba,Ca)(Ti,Zr)O$_3$.

When the Bi is present in the grain boundary, the friction between the crystal grains is reduced, and the mechanical quality factor is increased. When the Bi is formed into a solid solution in (Ba,Ca)(Ti,Zr)O$_3$ having a perovskite structure, the $T_{ot}$ and $T_{to}$ are decreased. Accordingly, the temperature dependence of the piezoelectric constant within the operating temperature range is lowered, and the mechanical quality factor can be further improved.

In order to facilitate the manufacturing of the piezoelectric ceramics of the present disclosure and adjusting the physical properties of the piezoelectric ceramics of the present disclosure, 1 mol % or less of the Ba and the Ca may be substituted with a divalent metal element such as Sr. Similarly, 1 mol % or less of the Ti and the Zr may be substituted with a tetravalent metal element such as Hf.

In the piezoelectric ceramics of the present disclosure, it is preferred that the fluctuation rate of the electromechanical coupling coefficient $k_{31}$ within a temperature range of 0° C. or more and 60° C. or less be 35% or less.

When the piezoelectric ceramics is used indoors, the temperature of the piezoelectric ceramics including the heat generation at the time of drive mainly falls within a temperature range of 0° C. or more and 60° C. or less. When the fluctuation rate of the electromechanical coupling coefficient $k_{31}$ is 35% or less within the above-mentioned temperature range, a fluctuation in piezoelectric performance for each temperature is small, and it is not required to change the control method of the piezoelectric ceramics in accordance with a change in temperature.

It is preferred that the piezoelectric ceramics of the present disclosure have an average equivalent circle diameter of 1 μm or more and 10 μm or less. When the average equivalent circle diameter of the piezoelectric ceramics of the present disclosure is set to 10 μm or less, chipping at the time of cutting and abrasion is reduced.

The "particle diameter" as used herein represents a "projected area equivalent circle diameter" generally referred to in a microscopic observation method, and represents a diameter of a perfect circle having the same area as that of the projected area of the crystal grain. In the present disclosure, a method of measuring a particle diameter is not particularly limited. For example, the particle diameter can be obtained by subjecting a photographic image, which is obtained by photographing the surface of a piezoelectric ceramics with a polarizing microscope or a scanning electron microscope, to image processing. The optimum magnification varies depending on a target particle diameter, and hence an optical microscope and an electron microscope may be used properly depending on the case. The equivalent circle diameter may be obtained from an image of an abraded surface or a cross-section instead of the surface of a material.

The relative density of the piezoelectric ceramics of the present disclosure is preferably 93% or more and 100% or less. The density of the sintered compact can be measured by, for example, the Archimedes method. In the present disclosure, when a ratio of measured density ($\rho_{meas.}$) to theoretical density ($\rho_{calc.}$) obtained based on the composition and the lattice constant of the sintered impact, that is, relative density ($\rho_{calc.}/\rho_{meas.}$) is 93% or more, it can be said that the relative density is sufficiently high as the piezoelectric ceramics.

The piezoelectric ceramics of the present disclosure has a thickness of preferably 10 μm or more, more preferably 50 μm or more. When the thickness of the piezoelectric ceramics is set to 10 μm or more, the abrading step becomes easy, and desired roughness Ra is obtained. When the thickness of the piezoelectric ceramics is set to 50 μm or more, damage at the time of processing such as abrasion is less liable to occur.

The piezoelectric element of the present disclosure is characterized by including a plurality of electrodes and a piezoelectric ceramics.

Now, the piezoelectric element using the piezoelectric ceramics of the present disclosure is described. FIG. 1 is a schematic view for illustrating a configuration of a piezoelectric element according to one embodiment of the present disclosure. In FIG. 1, as the plurality of electrodes, there are provided a first electrode 1 formed on a first surface of a piezoelectric ceramics 2 and a second electrode 3 divided into two formed on a surface of the piezoelectric ceramics 2 on an opposite side to the surface on which the first electrode 1 is formed. The piezoelectric element according to the present disclosure is a piezoelectric element including the plurality of electrodes and the piezoelectric ceramics, and is characterized in that the piezoelectric ceramics 2 is the piezoelectric ceramics of the present disclosure.

The piezoelectric ceramics according to the present disclosure can be evaluated for an electromechanical coupling coefficient and a mechanical quality factor thereof by forming the piezoelectric element having the plurality of electrodes. The first electrode and the second electrode are each formed of a conductive layer having a thickness of from about 5 nm to about 10 μm.

The material for each of the first electrode and the second electrode may be made of one kind or may be made of a laminate of two or more kinds. In addition, the first electrode and the second electrode may be made of different materials.

A polarization method for the piezoelectric element is not particularly limited. The polarization treatment may be performed in the air or may be performed in silicone oil. A temperature at which the polarization is performed is preferably a temperature of from 60° C. to 150° C. However, an optimum condition slightly varies depending on the composition of a piezoelectric ceramics forming the element. An electric field to be applied for performing the polarization treatment is preferably from 600 V/mm to 2.0 kV/mm.

The electromechanical coupling coefficient and the mechanical quality factor of the piezoelectric element can be calculated from measurement results of a resonance frequency and an antiresonance frequency obtained through use of a commercially available impedance analyzer based on the Japan Electronics and Information Technology Industries Association standards (JEITA EM-4501). This method is hereinafter referred to as "resonance-antiresonance method".

In addition, there is no particular limitation on a raw material for adjusting the "a", which indicates the ratio $\{a=(Ba+Ca)/(Zr+Ti)\}$ of the sum of the numbers of moles of the Ti and the Zr to the sum of the numbers of moles of the Ba and the Ca of the piezoelectric ceramics according to the present disclosure. The effect is the same irrespective of whether a Ba compound, a Ca compound, a Ti compound, or a Zr compound is used as the raw material.

The piezoelectric element according to the present disclosure also encompasses a laminated piezoelectric element in which a large number of piezoelectric ceramics of the present disclosure are laminated, or a laminated piezoelectric element in which a large number of piezoelectric elements are stacked to form a rod so that displacement in a thickness direction is utilized.

Next, an ultrasonic motor using the piezoelectric element of the present disclosure is described.

(Ultrasonic Motor)

Figure 2:
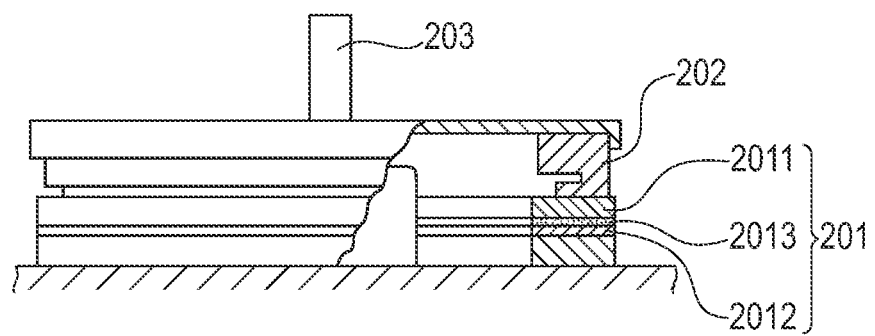
FIG. 2 is a schematic view for illustrating a configuration of an ultrasonic motor according to one embodiment of the present disclosure.

An ultrasonic motor according to the present disclosure is characterized by including at least a vibrating body in which the piezoelectric element is arranged, and a moving body (contact body) to be brought into contact with the vibrating body and relatively movable. FIG. 2 is a schematic view for illustrating a configuration of an ultrasonic motor according to one embodiment of the present disclosure. FIG. 2 is an illustration of an ultrasonic motor in which the piezoelectric element of the present disclosure is formed of a single plate. The ultrasonic motor includes an oscillator 201, a rotor 202, which is brought into contact with the sliding surface of the oscillator 201 with a pressure applied by a pressurizing spring (not shown), and an output shaft 203 arranged so as to be integrated with the rotor 202. The oscillator 201 is formed of a metal elastic ring 2011, a piezoelectric ceramics 2012 of the present disclosure, and an organic adhesive 2013 for bonding the piezoelectric element 2012 to the elastic ring 2011 (such as an epoxy- or cyanoacrylate-based adhesive). The piezoelectric element 2012 of the present disclosure is formed of a piezoelectric ceramics sandwiched between a first electrode (not shown) and a second electrode (not shown). The application of two alternating voltages different from each other in phase by an odd multiple of $\pi/2$ to the piezoelectric element of the present disclosure results in the generation of a flexural traveling wave in the oscillator 201, and hence each point on the sliding surface of the oscillator 201 undergoes an elliptical motion. When the rotor 202 is brought into press contact with the sliding surface of the oscillator 201, the rotor 202 receives a frictional force from the oscillator 201 to rotate in the direction opposite to the flexural traveling wave. A body to be driven (not shown) is joined to the output shaft 203, and is driven by the rotary force of the rotor 202. The application of a voltage to the piezoelectric ceramics results in the expansion and contraction of the piezoelectric material due to a transverse piezoelectric effect. When an elastic body, such as a metal, is bonded to the piezoelectric element through an adhesive or the like, the elastic body is bent by the expansion and contraction of the piezoelectric ceramics through the adhesive. The ultrasonic motor of the kind described in the foregoing utilizes this principle.

(Optical Apparatus)

Next, an optical apparatus of the present disclosure is described. The optical apparatus of the present disclosure includes a drive unit including the ultrasonic motor.

Figure 3A:
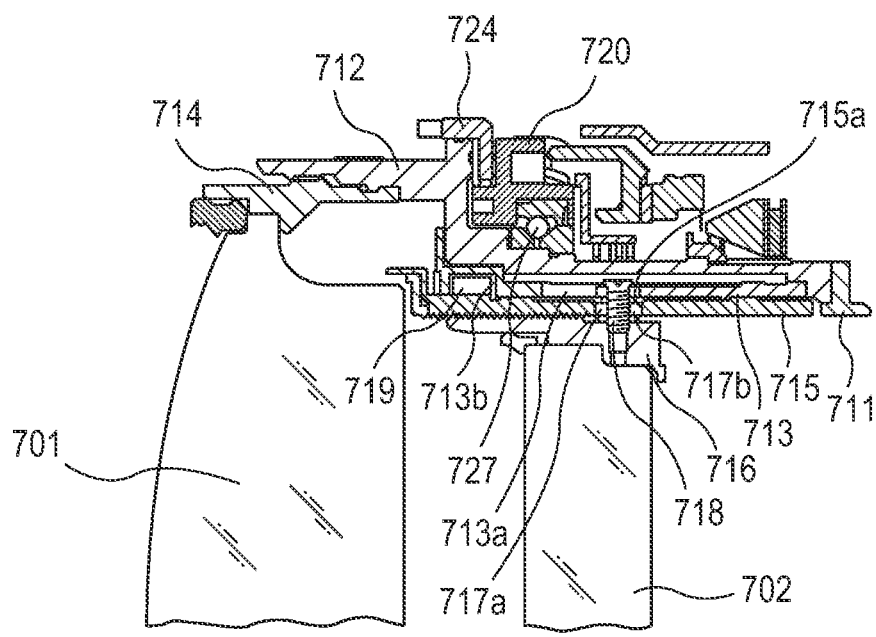
FIG. 3A is a schematic view for illustrating an optical apparatus according to one embodiment of the present disclosure.
Figure 3B:
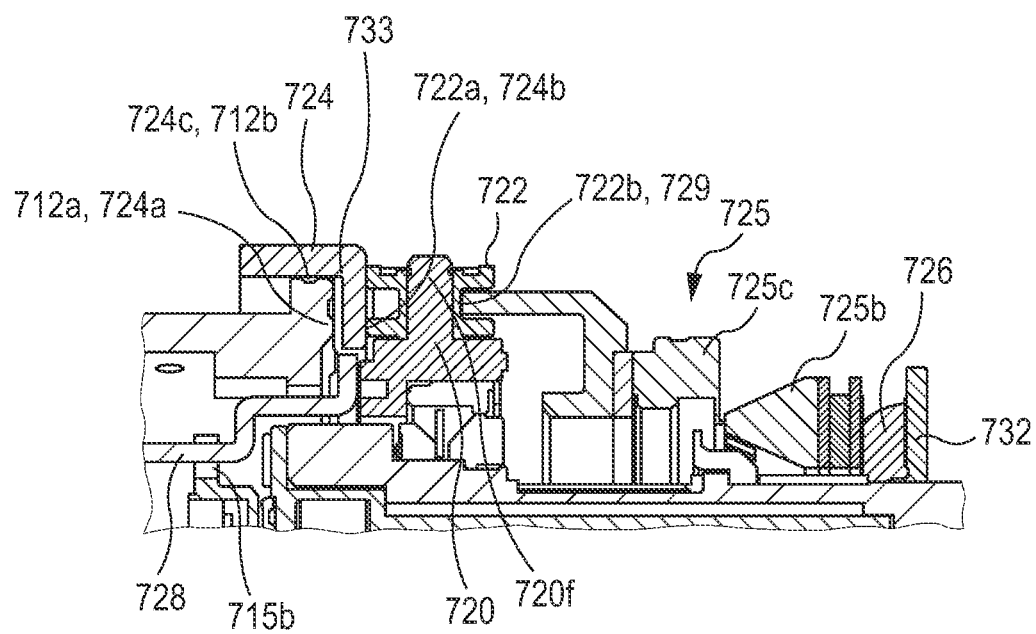
FIG. 3B is a schematic view for illustrating the optical apparatus according to one embodiment of the present disclosure.
Figure 4:
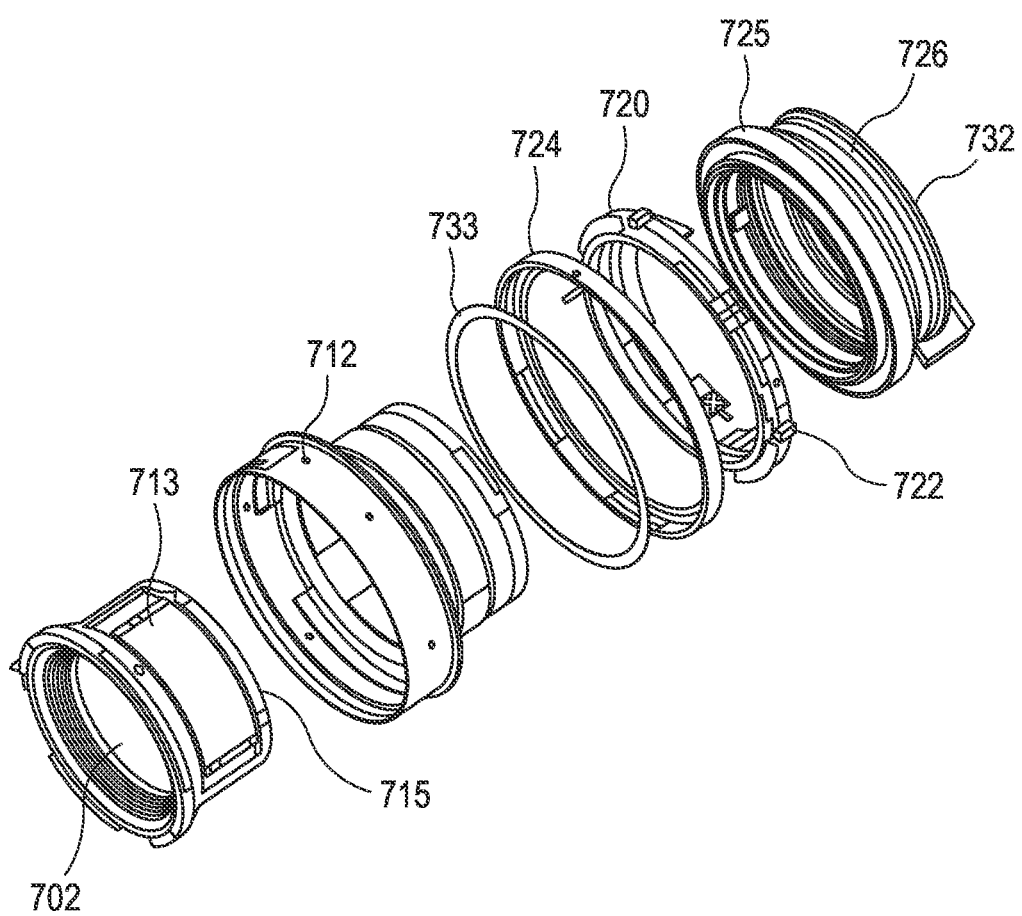
FIG. 4 is a schematic view for illustrating the optical apparatus according to one embodiment of the present disclosure.

FIG. 3A and FIG. 3B are each a sectional view of main parts of an interchangeable lens barrel for a single-lens reflex camera as an example of an optical apparatus according to an exemplary embodiment of the present disclosure. In addition, FIG. 4 is an exploded perspective view of the interchangeable lens barrel for the single-lens reflex camera as the example of the optical apparatus according to the preferred embodiment of the present disclosure. A fixed barrel 712, a linear guide barrel 713, and a front unit barrel 714 are fixed to an attaching/detaching mount 711 for a camera. Those members are fixed members of the interchangeable lens barrel.

A linear guide groove 713a in an optical axis direction for a focus lens 702 is formed on the linear guide barrel 713. Cam rollers 717a and 717b protruding outward in a radial direction are fixed to a rear unit barrel 716 holding the focus lens 702 via axial screws 718, and the cam roller 717a is fitted in the linear guide groove 713a.

A cam ring 715 is fitted on the inner periphery of the linear guide barrel 713 in a rotatable manner. Relative movement between the linear guide barrel 713 and the cam ring 715 in the optical axis direction is restricted because a roller 719 fixed to the cam ring 715 is fitted in an annular groove 713b of the linear guide barrel 713. A cam groove 715a for the focus lens 702 is formed on the cam ring 715, and the above-mentioned cam roller 717b is simultaneously fitted in the cam groove 715a. On the outer peripheral side of the fixed barrel 712, there is arranged a rotation transmission ring 720 held by a ball race 727 in a rotatable manner at a constant position with respect to the fixed barrel 712. The rotation transmission ring 720 has shafts 720f extending radially from the rotation transmission ring 720, and rollers 722 are held by the shafts 720f in a rotatable manner. A large diameter part 722a of the roller 722 is brought into contact with a mount side end surface 724b of a manual focus ring 724. In addition, a small diameter part 722b of the roller 722 is brought into contact with a joining member 729. Six rollers 722 are arranged on the outer periphery of the rotation transmission ring 720 at regular intervals, and each roller is arranged in the relationship as described above.

A low friction sheet (washer member) 733 is arranged on an inner diameter part of the manual focus ring 724, and this low friction sheet is sandwiched between a mount side end surface 712a of the fixed barrel 712 and a front side end surface 724a of the manual focus ring 724. In addition, an outer diameter surface of the low friction sheet 733 is formed in a ring shape so as to be circumferentially fitted on an inner diameter part 724c of the manual focus ring 724. Further, the inner diameter part 724c of the manual focus ring 724 is circumferentially fitted on an outer diameter part 712b of the fixed barrel 712. The low friction sheet 733 has a role of reducing friction in a rotation ring mechanism in which the manual focus ring 724 rotates relatively to the fixed barrel 712 about the optical axis.

The large diameter part 722a of the roller 722 is brought into contact with the mount side end surface 724b of the manual focus ring under a state in which a pressure is applied by a pressing force of a waved washer 726 pressing an ultrasonic motor 725 to the front of the lens. In addition, similarly, the small diameter part 722b of the roller 722 is brought into contact with the joining member 729 under a state in which an appropriate pressure is applied by a pressing force of the waved washer 726 pressing the ultrasonic motor 725 to the front of the lens. Movement of the waved washer 726 in the mount direction is restricted by a washer 732 connected to the fixed barrel 712 by bayonet joint. A spring force (biasing force) generated by the waved washer 726 is transmitted to the ultrasonic motor 725, and further to the roller 722, to be a force for the manual focus ring 724 to press the mount side end surface 712a of the fixed barrel 712. In other words, the manual focus ring 724 is integrated under a state in which the manual focus ring 724 is pressed to the mount side end surface 712a of the fixed barrel 712 via the low friction sheet 733.

Accordingly, when a control unit (not shown) drives the ultrasonic motor 725 to rotate with respect to the fixed barrel 712, the rollers 722 rotate about the shafts 720f because the joining member 729 is brought into frictional contact with the small diameter parts 722b of the rollers 722. As a result of the rotation of the rollers 722 about the shafts 720f, the rotation transmission ring 720 rotates about the optical axis (automatic focus operation).

In addition, when a manual operation input portion (not shown) gives a rotation force about the optical axis to the manual focus ring 724, the following action occurs. That is, the rollers 722 rotate about the shafts 720f by friction force because the mount side end surface 724b of the manual focus ring 724 is brought into contact by pressure to the large diameter parts 722a of the rollers 722. When the large diameter parts 722a of the rollers 722 rotate about the shafts 720f, the rotation transmission ring 720 rotates about the optical axis. In this case, the ultrasonic motor 725 does not rotate because of a friction retaining force between a rotor 725c and a stator 725b (manual focus operation).

Two focus keys 728 are mounted to the rotation transmission ring 720 at opposing positions, and the focus key 728 is fitted to a notch portion 715b arranged on the tip of the cam ring 715. Accordingly, when the automatic focus operation or the manual focus operation is performed so that the rotation transmission ring 720 is rotated about the optical axis, the rotation force is transmitted to the cam ring 715 via the focus key 728. When the cam ring is rotated about the optical axis, the rear unit barrel 716 whose rotation is restricted by the cam roller 717a and the linear guide groove 713a is moved forward and backward along the cam groove 715a of the cam ring 715 by the cam roller 717b. Thus, the focus lens 702 is driven, and the focus operation is performed.

While the interchangeable lens barrel for the single-lens reflex camera has been described as the optical apparatus of the present disclosure, the optical apparatus of the present disclosure can be applied to any optical apparatus including the drive unit including the ultrasonic motor, regardless of a type of the camera, including a compact camera, an electronic still camera, a personal digital assistant with a camera, and the like.

(Vibration Device and Dust Removing Device)

A vibration device used, for example, for conveying and removing particles, powder, and droplets are widely used in an electronic apparatus and the like.

Now, as an example of a vibration device of the present disclosure, a dust removing device using the piezoelectric element of the present disclosure is described.

The dust removing device according to the present disclosure is characterized by including a vibrating body in which the piezoelectric element or the laminated piezoelectric element is arranged on a vibrating plate, that is, by including the vibration device in a vibrating portion.

Figure 5A:
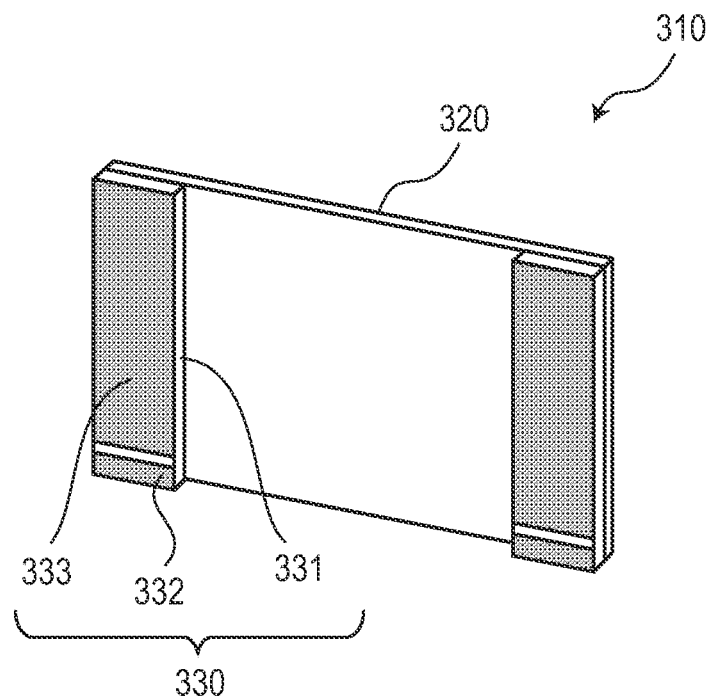
FIG. 5A is a schematic view for illustrating one embodiment in the case where a vibration device of the present disclosure is used as a dust removing device.
Figure 5B:
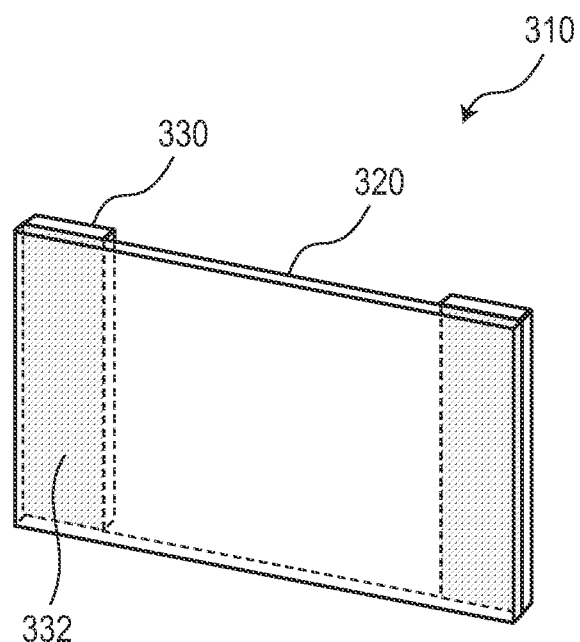
FIG. 5B is a schematic view for illustrating one embodiment in the case where the vibration device of the present disclosure is used as the dust removing device.

FIG. 5A and FIG. 5B are each a schematic view for illustrating a dust removing device according to one embodiment of the present disclosure. A dust removing device 310 includes plate-like piezoelectric elements 330 and a vibrating plate 320. A material for the vibrating plate 320 is not limited. When the dust removing device 310 is used for an optical apparatus, a light transmissive material or a light reflective material may be used as the vibrating plate 320.

Figure 6A:
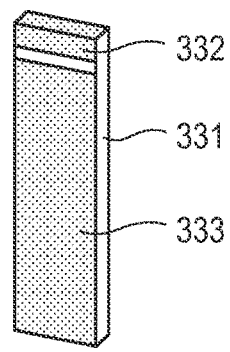
FIG. 6A is a schematic view for illustrating a configuration of a piezoelectric element in the dust removing device of the present disclosure.
Figure 6B:
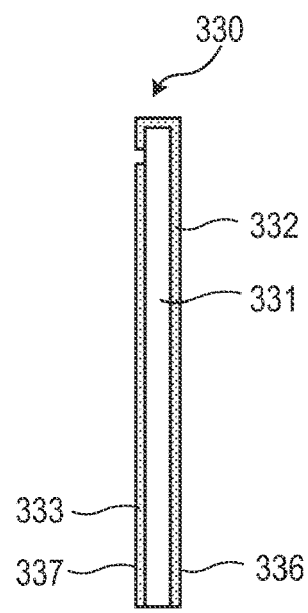
FIG. 6B is a schematic view for illustrating a configuration of the piezoelectric element in the dust removing device of the present disclosure.
Figure 6C:
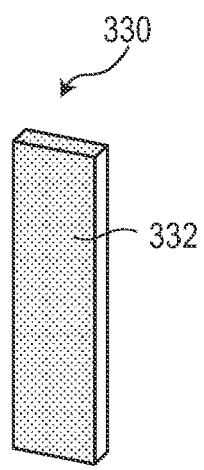
FIG. 6C is a schematic view for illustrating a configuration of the piezoelectric element in the dust removing device of the present disclosure.

FIG. 6A, FIG. 6B, and FIG. 6C are each a schematic view for illustrating a configuration of the piezoelectric element 330 in FIG. 5A and FIG. 5B. In FIG. 6A and FIG. 6C, configurations of front and back surfaces of the piezoelectric element 330 are illustrated. In FIG. 6B, a configuration of a side surface is illustrated. As illustrated in FIG. 6A, the piezoelectric element 330 includes a piezoelectric ceramics 331, a first electrode 332, and a second electrode 333, and the first electrode 332 and the second electrode 333 are each arranged so as to be opposed to a plate surface of the piezoelectric ceramics 331.

In FIG. 6C, a surface on which the first electrode 332 protruding in front of the piezoelectric element 330 is installed is defined as a first electrode surface 336, and in FIG. 6A, a surface on which the second electrode 333 protruding in front of the piezoelectric element 330 is installed is defined as a second electrode surface 337.

Herein, the electrode surface in the present disclosure refers to the surface of the piezoelectric element on which the electrode is installed, and the first electrode 332 may wrap around the second electrode surface 337, for example, as illustrated in FIG. 6B.

As illustrated in FIG. 5A and FIG. 5B, in the piezoelectric elements 330 and the vibrating plate 320, the first electrode surface 336 of each of the piezoelectric elements 330 is fixed to a plate surface of the vibrating plate 320. Then, a stress is generated between the piezoelectric element 330 and the vibrating plate 320 by driving the piezoelectric element 330, to thereby generate out-of-plane vibration in the vibrating plate 320. The dust removing device 310 of the present disclosure is a device configured to remove foreign matter, such as dust, adhering to the surface of the vibrating plate 320 through the out-of-plane vibration of the vibrating plate 320. The out-of-plane vibration means elastic vibration that displaces the vibrating plate 320 into an optical axis direction, that is, a thickness direction of the vibrating plate 320.

Figure 7A:
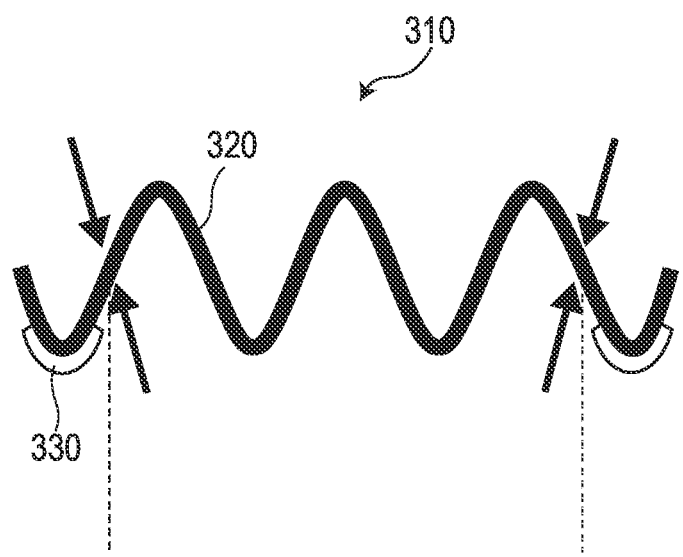
FIG. 7A is a schematic diagram for illustrating the vibration principle of the dust removing device of the present disclosure.
Figure 7B:
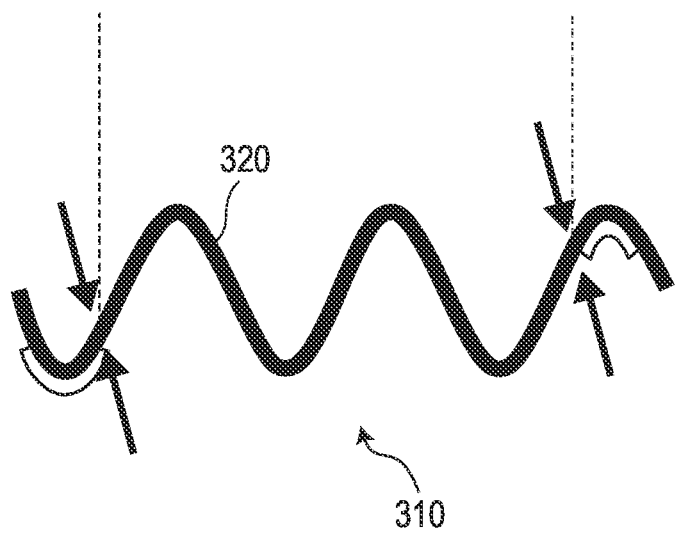
FIG. 7B is a schematic diagram for illustrating the vibration principle of the dust removing device of the present disclosure.

FIG. 7A and FIG. 7B are each a schematic diagram for illustrating the vibration principle of the dust removing device 310 of the present disclosure. In FIG. 7A, there is illustrated a state in which the out-of-plane vibration is generated in the vibrating plate 320 by applying AC voltages having the same phase to a pair of left and right piezoelectric elements 330, respectively. The polarization direction of the piezoelectric ceramics forming the pair of left and right piezoelectric elements 330 is the same as the thickness direction of the piezoelectric elements 330, and the dust removing device 310 is driven in the seventh vibration mode. In FIG. 7B, there is illustrated a state in which the out-of-plane vibration is generated in the vibrating plate 320 by applying AC voltages having opposite phases that are opposite by 180° to the pair of left and right piezoelectric elements 330, respectively. The dust removing device 310 is driven in the sixth vibration mode. The dust removing device 310 of the present disclosure is a device capable of effectively removing dust adhering to the surface of the vibrating plate 320 by using at least two vibration modes properly depending on the case. In FIG. 7A and FIG. 7B, parts indicated by the arrows indicate fixed portions between the piezoelectric elements 330 and the vibrating plate 320.

(Image Pickup Apparatus)

Figure 8:
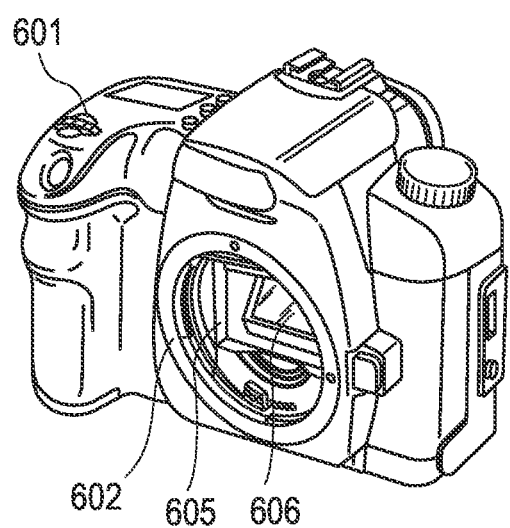
FIG. 8 is a schematic view for illustrating an image pickup apparatus according to one embodiment of the present disclosure.
Figure 9:
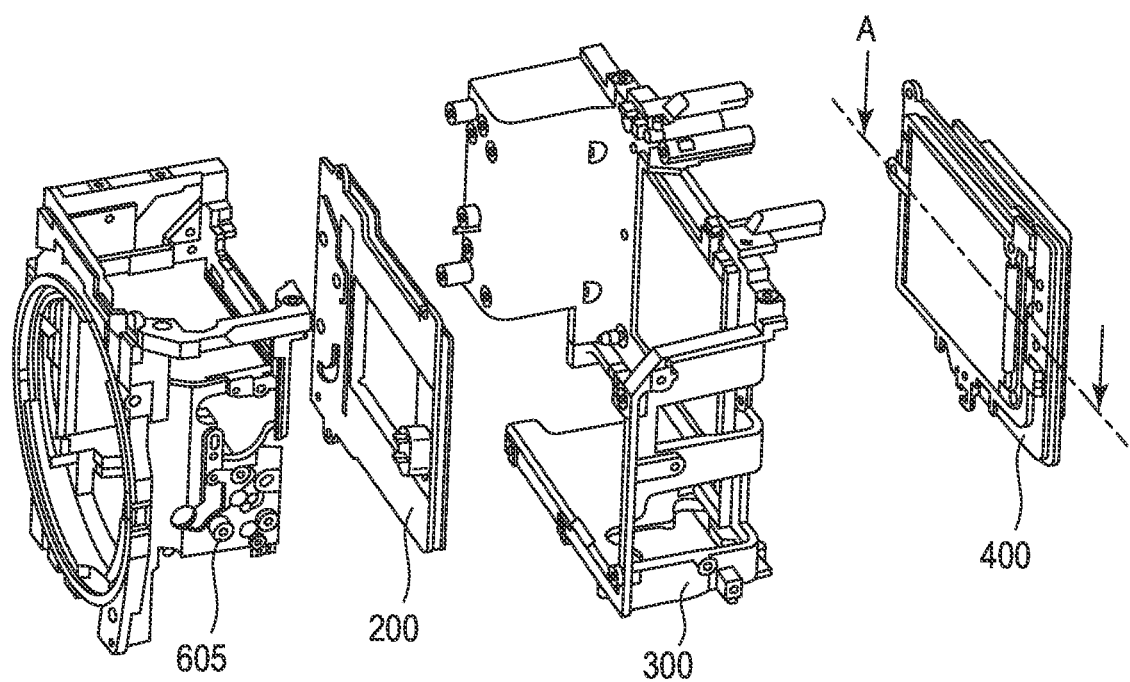
FIG. 9 is a schematic view for illustrating the image pickup apparatus according to one embodiment of the present disclosure.

Next, an image pickup apparatus of the present disclosure is described. The image pickup apparatus of the present disclosure is an image pickup apparatus including at least the dust removing device and an image pickup element unit, and is characterized in that the vibrating plate of the dust removing device is provided on a light receiving surface side of the image pickup element unit. FIG. 8 and FIG. 9 are each a view for illustrating a digital single-lens reflex camera that is an example of the image pickup apparatus according to an exemplary embodiment of the present disclosure.

FIG. 8 is a front side perspective view of a camera main body 601 when viewed from an object side, for illustrating a state in which a photographing lens unit is removed. FIG. 9 is an exploded perspective view of a schematic configuration of an inner portion of the camera for illustrating peripheral structures of the dust removing device of the present disclosure and an image pickup unit 400.

A mirror box 605 configured to guide a photographing luminous flux having passed through a photographing lens is provided in the camera main body 601, and a main mirror (quick return mirror) 606 is arranged in the mirror box 605. The main mirror 606 may have a state of being held at an angle of 45° with respect to a photographing optical axis in order to guide the photographing luminous flux in a direction of a pentadha mirror (not shown), and a state of being held at a position retracted from the photographing luminous flux in order to guide the photographing luminous flux in a direction of an image pickup element (not shown).

On the object side of a main body chassis 300 serving as a skeleton of the camera main body, the mirror box 605 and a shutter unit 200 are arranged in the stated order from the object side. In addition, the image pickup unit 400 is arranged on a photographer side of the main body chassis 300. The image pickup unit 400 is installed so that an image pickup surface of the image pickup element is adjusted to be parallel to a mounting surface of a mount portion 602 serving as a reference for mounting the photographing lens unit at a predetermined distance.

Herein, the digital single-lens reflex camera has been described as the image pickup apparatus of the present disclosure, but for example, a camera with an interchangeable photographing lens unit, such as a mirrorless digital single-lens camera without the mirror box 605, may be used. In addition, the image pickup apparatus of the present disclosure can also be applied to a device in which it is required to remove dust adhering to the surface of an optical component, in particular, among various image pickup apparatus, such as a video camera with an interchangeable photographing lens unit, a copying machine, a fax machine, and a scanner, or electronic and electrical devices including image pickup apparatus.

(Ultrasonic Probe)

Next, an ultrasonic probe of the present disclosure is described. The ultrasonic probe of the present disclosure is characterized by including the piezoelectric element, in which the piezoelectric element is configured to transmit and receive a signal.

Figure 10:
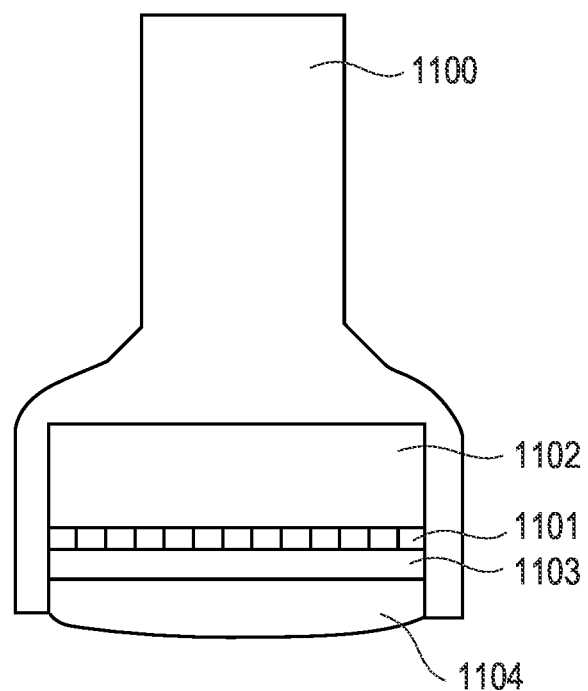
FIG. 10 is a schematic view for illustrating an ultrasonic probe according to one embodiment of the present disclosure.

FIG. 10 is a schematic sectional view for illustrating the ultrasonic probe according to one embodiment of the present disclosure.

An ultrasonic probe 1100 of FIG. 10 includes a housing, a plurality of piezoelectric elements 1101, a backing material 1102, an acoustic matching layer 1103, and an acoustic lens 1104. As illustrated in FIG. 10, the plurality of piezoelectric elements 1101 are arranged on the backing material 1102 so as to adhere thereto, and the acoustic matching layer 1103 configured to match an acoustic impedance is formed on each surface serving as a transmitting/receiving surface of the piezoelectric elements 1101 on a side opposite to the backing material 1102.

The acoustic matching layer 1103 may be a single layer or a plurality of layers, preferably two or more layers. As a material to be used for the acoustic matching layer 1103, there may be used, for example, carbon, aluminum, an aluminum alloy (e.g., an AL-Mg alloy), a magnesium alloy, Macor glass, glass, fused quartz, copper graphite, polyethylene, polypropylene, polycarbonate, an ABC resin, polyphenylene ether, an ABS resin, an AAS resin, an AES resin, nylon, polyamide imide, polyethylene terephthalate, polycarbonate, an epoxy resin, or a urethane resin.

In addition, as the backing material 1102, there may be used, for example, a thermoplastic resin, such as natural rubber, ferrite rubber, an epoxy resin, vinyl chloride, polyvinyl butyral, an ABS resin, polyurethane, polyvinyl alcohol, polyethylene, polypropylene, polyacetal, polyethylene terephthalate, a fluorine resin, polyethylene glycol, or polyethylene terephthalate, a product obtained by adding metal powder thereto, or a superhard material, such as tungsten carbide.

The piezoelectric element 1101 may be integrated or may be divided into a plurality of pieces. In FIG. 10, there is illustrated an example of a case in which the piezoelectric element 1101 is provided so as to be divided. A flexible cable (not shown) is connected to electrodes of respective piezoelectric elements 1101 so that signals transmitted and received by the piezoelectric elements can be input and output. The acoustic lens 1104 adheres to the acoustic matching layer 1103. The acoustic lens 1104 is a member configured to converge ultrasonic waves transmitted from the piezoelectric elements 1101 toward the object, and has an arc shape in the example of FIG. 10. As a material for the acoustic lens 1104, for example, a rubber containing a silicone-based resin (rubber) as a main component is generally used.

When the ultrasonic probe 1100 is used, an AC voltage is applied to the piezoelectric elements 1101 through the flexible cable, and the piezoelectric elements 1101 are vibrated by the piezoelectric effect to transmit the ultrasonic waves from the piezoelectric elements 1101. In this case, when the acoustic impedance of the object which the ultrasonic waves are applied is small, or when the ultrasonic waves are applied to the object through water or air, reflected waves caused by a great change in acoustic impedance can be suppressed due to the presence of the acoustic matching layer 1103, and the ultrasonic waves to the object can be efficiently radiated thereto. Then, at the time of reception, the piezoelectric elements 1101 are vibrated with the ultrasonic waves reflected from the inside of the object, and this vibration is electrically converted by the piezoelectric effect to obtain a reception signal. At the time of transmission and reception, the conversion of electrical energy and mechanical energy is performed, and the conversion efficiency in this case depends on the magnitude of the electromechanical coupling coefficient.

(Ultrasonic Diagnostic Apparatus)

Figure 11:
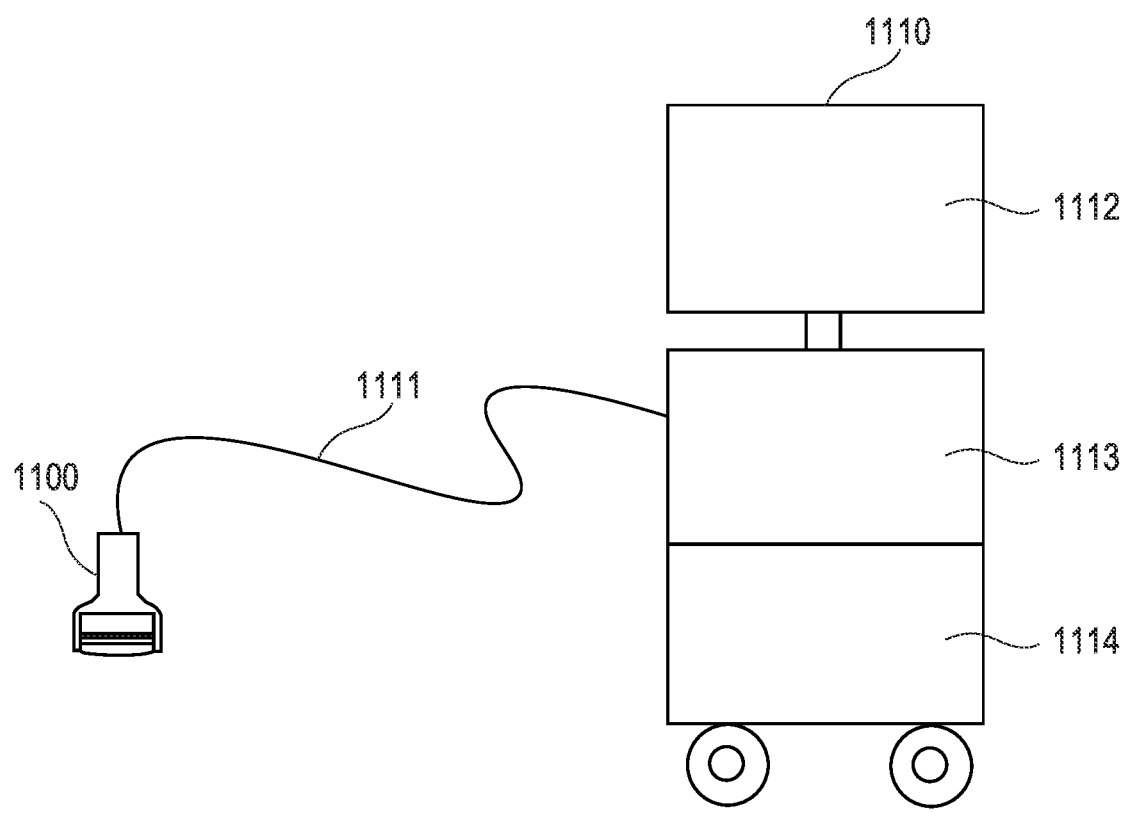
FIG. 11 is a schematic view for illustrating an ultrasonic diagnostic apparatus according to one embodiment of the present disclosure.

Next, an ultrasonic diagnostic apparatus of the present disclosure is described. The ultrasonic diagnostic apparatus of the present disclosure is characterized by including at least the ultrasonic probe and an image display portion. FIG. 11 is a schematic view for illustrating the ultrasonic diagnostic apparatus according to one embodiment of the present disclosure. An ultrasonic diagnostic apparatus 1110 of FIG. 11 includes the ultrasonic probe 1100, a cable 1111, a drive control unit 1113, and an image display portion. The flexible cable of the ultrasonic probe 1100 and the drive control unit 1113 are connected to each other through the cable 1111, and an AC voltage is applied from the drive control unit 1113 to the piezoelectric elements 1101 of the ultrasonic probe 1100 through the cable 1111. When the ultrasonic waves are radiated to the inside of the object from the ultrasonic probe 1100, the ultrasonic waves reflected from the inside of the object are converted into electric signals again by the ultrasonic probe 1100 and input to an image processing unit 1114 through the cable 1111. In the image processing unit 1114, image data is created through calculation from changes in delay time and signal intensity with respect to the AC voltage output from the drive control unit 1113. The created image data is output to the image display portion 1112.

(Electronic Apparatus)

Next, an electronic apparatus of the present disclosure is described.

The electronic apparatus of the present disclosure includes a member and a piezoelectric element or a laminated piezoelectric element arranged on the member.

The electronic apparatus of the present disclosure may be formed as a piezoelectric acoustic component including the piezoelectric element or the laminated piezoelectric element. The piezoelectric acoustic component encompasses a speaker, a buzzer, a microphone, and a surface acoustic wave (SAW) element.

Figure 12:
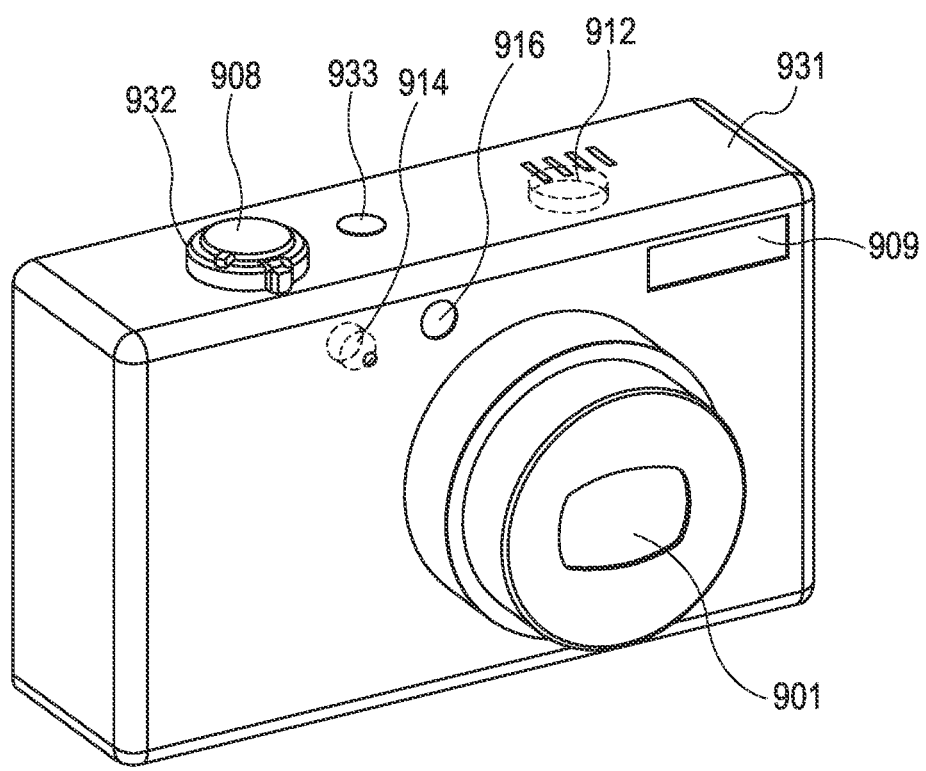
FIG. 12 is a schematic view for illustrating an electronic apparatus according to one embodiment of the present disclosure.

FIG. 12 is a general perspective view of a main body 931 of a digital camera as an example of an electronic apparatus according to a preferred embodiment of the present disclosure, as viewed from the front. An optical apparatus 901, a microphone 914, a stroboscopic light emission unit 909, and a fill light unit 916 are arranged on a front surface of the main body 931. The microphone 914 is installed in the main body, and hence is illustrated by a broken line. In the front of the microphone 914, there is a hole shape provided for collecting external sound.

A power button 933, a speaker 912, a zoom lever 932, and a release button 908 for performing a focus operation are arranged on the top surface of the main body 931. The speaker 912 is installed in the main body 931, and hence is illustrated by a broken line. In the front of the speaker 912, there is a hole shape provided for transmitting sound to the outside.

The piezoelectric acoustic component of the present disclosure is used for at least one of the microphone 914, the speaker 912, or the surface acoustic wave element.

While the digital camera has been described as the electronic apparatus of the present disclosure, the electronic apparatus of the present disclosure can also be applied to various types of the electronic apparatus including the piezoelectric acoustic component, such as a sound reproduction device, a sound recording device, a cellular phone, or an information terminal.

As described above, the piezoelectric element of the present disclosure is suitably used in an ultrasonic motor, an optical apparatus, a vibration device, a dust removing device, an image pickup apparatus, an ultrasonic probe, an ultrasonic diagnostic apparatus, and an electronic apparatus.

Through the use of the piezoelectric element of the present disclosure, there can be provided the ultrasonic motor having driving efficiency comparable to or higher than that in the case of using the piezoelectric element containing lead.

Through the use of the ultrasonic motor of the present disclosure, there can be provided the optical apparatus having operation speed and operation efficiency comparable to or higher than those in the case of using the piezoelectric element containing lead.

Through use of the piezoelectric element of the present disclosure, there can be provided the vibration device having vibration ability comparable to or higher than that in the case of using the piezoelectric element containing lead.

Through use of the vibration device of the present disclosure, there can be provided the dust removing device having dust removing efficiency comparable to or higher than that in the case of using the piezoelectric element containing lead.

Through use of the dust removing device of the present disclosure, there can be provided the image pickup apparatus having a dust removing function comparable to or higher than that in the case of using the piezoelectric element containing lead.

Through use of the piezoelectric element of the present disclosure, there can be provided the ultrasonic probe having transmitting/receiving performance comparable to or higher than that in the case of using the piezoelectric element containing lead.

Through use of the ultrasonic probe of the present disclosure, there can be provided the ultrasonic diagnostic apparatus having driving efficiency comparable to or higher than that in the case of using the piezoelectric element containing lead.

Through the use of the piezoelectric acoustic component including the piezoelectric element of the present disclosure, there can be provided the electronic apparatus having sound producing performance comparable to or higher than that in the case of using the piezoelectric element containing lead.

The piezoelectric ceramics and the piezoelectric element of the present disclosure may be used in devices, such as a motor, a liquid discharge head, a liquid discharge device, a piezoelectric actuator, a piezoelectric sensor, and a ferroelectric memory, in addition to the above-mentioned devices.

EXAMPLES

The present disclosure is hereinafter described more specifically by way of Examples. However, the present disclosure is not limited to the following Examples.

The piezoelectric ceramics and the piezoelectric element of the present disclosure were produced by the following methods.

Example 1

As raw material powders, barium titanate ($BaTiO_3$, Ba/Ti=0.9985) having an average particle diameter of 100 nm, calcium titanate ($CaTiO_3$, Ca/Ti=0.9978), calcium zirconate ($CaZrO_3$, Ca/Zr=0.999), bismuth oxide ($Bi_2O_3$), trimanganese tetraoxide ($Mn_3O_4$), and barium carbonate for adjusting a ratio "a" of a sum of the numbers of moles of Ti and Zr to a sum of the numbers of moles of Ba and Ca were used. Those raw material powders were weighed so as to obtain a ratio of the composition formula $(Ba_{0.86}, Ca_{0.14})_{1.002}(Ti_{0.93}, Zr_{0.07})O_3$ containing titanium and barium as main components. Mn was added to 100 parts by weight of this metal oxide so that the content of Mn became 0.16 part by weight in terms of a metal. Further, Bi was added to the metal oxide having Mn added thereto so that the content of Bi became 0.17 part by weight in terms of a metal, and the resultant was mixed by dry mixing for 24 hours through use of a ball mill. In order to granulate the obtained mixed powder, 3 parts by weight of a PVA binder based on the mixed powder was caused to adhere to the surface of the mixed powder through use of a spray dryer device.

Next, the obtained granulated powder was filled in a mold, and a molding pressure of 200 MPa was applied thereto using a press molding machine to produce a disc-shaped compact. The compact may be further pressurized using a cold isostatic pressing molding machine.

The obtained compact was placed in an electric furnace, kept at a maximum temperature of 1,300° C. for 5 hours, and sintered in an air atmosphere over a total of 24 hours to provide a disc-shaped sintered compact.

Then, the average equivalent circle diameter and the relative density of crystal grains forming the obtained sintered compact were evaluated. As a result, the average equivalent circle diameter was 8 μm, and the relative density was 98%. A polarizing microscope was mainly used for observing the crystal grains. A scanning electron microscope (SEM) was used for identifying the particle diameters of small crystal grains. The average equivalent circle diameter was calculated from the observation results. In addition, the relative density was evaluated through use of the theoretical density calculated from the lattice constant obtained from X-ray diffraction and the weighed composition, and the measured density by the Archimedes method.

Next, the obtained disc-shaped sintered compact was abraded on both surfaces through use of an abrasive machine while the size of abrasive grains was changed so that the thickness became 0.5 mm, and was finally subjected to chemical abrasion as finishing abrasion.

Then, the roughness Ra was measured on each of the abraded surfaces of the sintered compact. The measurement of the roughness Ra was performed through use of a stylus type surface profilometer with a stylus having a radius of curvature of 1 μm at a distal end portion thereof. The measurement conditions for the roughness Ra were a stylus scanning speed of 5 μm per second, a scanning distance of 200 μm, and a sampling rate of 200 Sa per second. As a result, the roughness Ra was 0.03 μm.

Next, the crystal structure of the abraded sintered compact was analyzed by X-ray diffraction. As a result, only peaks corresponding to a perovskite structure were observed.

Next, the composition of the sintered compact obtained by the ICP emission spectrochemical analysis was evaluated. As a result, the composition of Ba, Ca, Ti, Zr, Mn, and Bi after the sintering was matched with the weighed composition.

Next, the abraded sintered compact was placed in an electric furnace and held in the air at a maximum temperature of 990° C. for 120 minutes for annealing, to thereby obtain the piezoelectric ceramics of the present disclosure. Then, the surface roughness Ra was measured on each of the abraded surfaces of the obtained piezoelectric ceramics. The measurement of the roughness Ra was performed through use of a stylus type surface profilometer with a stylus having a radius of curvature of 1 μm at a distal end portion thereof. The measurement conditions for the roughness Ra were a stylus scanning speed of 5 μm per second, a scanning distance of 200 μm, and a sampling rate of 200 Sa per second. As a result, the surface roughness Ra after the annealing was 0.03 μm, which was the same as the surface roughness Ra before the annealing.

Next, gold electrodes each having a thickness of 400 nm were formed on the front and rear surfaces of the piezoelectric ceramics by DC sputtering. Titanium was formed into a film having a thickness of 30 nm as a contact layer between the electrodes and the ceramics. The ceramics with the electrodes was cut to produce a strip-shaped piezoelectric element of the present disclosure having a size of 10 mm×2.5 mm×0.5 mm. The surface of a hot plate was set to from 60° C. to 100° C., and an electric field of 1 kV/mm was applied to the obtained piezoelectric element on the hot plate for 30 minutes. Thus, polarization treatment was performed.

Next, as static characteristics of the piezoelectric element including the piezoelectric ceramics of the present disclosure, the electromechanical coupling coefficient $k_{31}$ and mechanical quality factor Qm of the piezoelectric element subjected to the polarization treatment were evaluated by a resonance-antiresonance method using an impedance analyzer (4294A manufactured by Agilent Technologies) at room temperature (25° C.).

The electromechanical coupling coefficient was measured in increments of 5° C. while the temperature of the sample was changed from 60° C. to 0° C. at a rate of 0.5° C. per minute, and a fluctuation rate of the electromechanical coupling coefficient $k_{31}$ within the temperature range of from 0° C. to 60° C. was derived in accordance with the following expression (4):

$$\text{Fluctuation rate of } k_{31} = 100 \times (k_{31MAX} - k_{31MIN}) \div k_{31ave} \quad (4)$$

where $k_{31MAX}$ represents a maximum value of $k_{31}$ during the temperature change, $k_{31MIN}$ represents a minimum value thereof, and $k_{31ave}$ represents an average value thereof.

Next, the power consumption of the strip-shaped piezoelectric element was evaluated. The power consumption was obtained by measuring, with a wattmeter, a value of the power consumption when an AC voltage was applied and the magnitude and frequency of the AC voltage were changed so that a displacement amount was 1.0 μm. In this case, the displacement amount was measured with a laser Doppler vibrometer. The power consumption at this time was 16 mW.

Examples 2 to 8

Piezoelectric ceramics and piezoelectric elements of Examples 2 to 8 of the present disclosure were obtained through the same steps as those in Example 1 except for the maximum temperature and the retention time of the maximum temperature in the abrading step and the annealing step.

In the abrading step, both surfaces were abraded through use of an abrasive machine while the size of abrasive grains was changed so that the thickness became 0.5 mm, and finally, finishing abrasion was performed through use of the abrasive machine with abrasive grains of #4,000. Specific numerical numbers of the maximum temperature and the retention time of the maximum temperature in the annealing step are shown in Table 1.

Subsequently, through the same steps as those in Example 1, the crystal structure of the piezoelectric ceramics forming the piezoelectric element of the present disclosure, the surface roughness Ra before and after the annealing, the electromechanical coupling coefficient $k_{31}$, and the fluctuation rate of $k_{31}$ within each temperature range, the mechanical quality factor Qm, and the power consumption were evaluated. The results are shown in Table 2.

Examples 9 to 11

Piezoelectric ceramics and piezoelectric elements of Examples 9 to 11 of the present disclosure were obtained through the same steps as those in Example 1 except for the abrading step, the annealing step, and the electrode forming method.

In the abrading step in each of Examples 9 to 11, both surfaces were abraded through use of an abrasive machine while the size of abrasive grains was changed so that the thickness became 0.5 mm, and finally, finishing abrasion was performed through use of the abrasive machine with abrasive grains of #4,000.

In addition, in each of Examples 9 to 11, a Ag electrode paste was applied to both surfaces of the piezoelectric ceramics by screen printing instead of a gold electrode paste. The resultant piezoelectric ceramics was placed in an electric furnace, and the annealing step was performed in an air atmosphere, to thereby obtain a piezoelectric element including the piezoelectric ceramics of the present disclosure. The annealing step was not performed before the Ag electrode paste was applied in Examples 9 and 10, and the annealing step was performed before the Ag electrode paste was applied, and hence the annealing step was performed substantially twice in Example 11.

The annealing temperature and retention time in the annealing step, and the temperature and time at the time of electrode baking are shown in Table 1. In addition, the surface roughness Ra after the annealing step was measured on the surface which was abraded and to which the electrodes were not applied. The measurement conditions for the surface roughness Ra were the same as those in Example 1.

Subsequently, through the same steps as those in Example 1, the crystal structure of the piezoelectric ceramics forming the piezoelectric element of the present disclosure, the surface roughness Ra before and after the annealing, the electromechanical coupling coefficient $k_{31}$, and the fluctuation rate of $k_{31}$ within each temperature range, the mechanical quality factor Qm, and the power consumption were evaluated. The results are shown in Table 2.

Example 12

As raw material powders, barium titanate ($BaTiO_3$, Ba/Ti=0.9985) having an average particle diameter of 100 nm, calcium titanate ($CaTiO_3$, Ca/Ti=0.9978), trimanganese tetraoxide ($Mn_3O_4$), and barium carbonate for adjusting a ratio "a" of a sum of the numbers of moles of Ti and Zr to a sum of the numbers of moles of Ba and Ca were used.

Those raw material powders were weighed so as to obtain a ratio of the composition formula $(Ba_{0.96},Ca_{0.04})_{1.005}TiO_3$ containing titanium and barium as main components. Mn was added to 100 parts by weight of this metal oxide so that the content of Mn became 0.10 part by weight in terms of a metal. Further, the metal oxide having Mn added thereto was mixed by dry mixing for 24 hours through use of a ball mill. In order to granulate the obtained mixed powder, 3 parts by weight of a PVA binder based on the mixed powder was caused to adhere to the surface of the mixed powder through use of a spray dryer device.

Next, the obtained granulated powder was filled in a mold, and a molding pressure of 200 MPa was applied thereto using a press molding machine to produce a disc-shaped compact. The compact may be further pressurized using a cold isostatic pressing molding machine.

The obtained compact was placed in an electric furnace, kept at a maximum temperature of 1,200° C. for 5 hours, and sintered in an air atmosphere over a total of 24 hours to provide a sintered compact.

Then, the average equivalent circle diameter and the relative density of crystal grains forming the obtained sintered compact were evaluated. As a result, the average equivalent circle diameter was 10 μm, and the relative density was 96%. A polarizing microscope was mainly used for observing the crystal grains. A scanning electron microscope (SEM) was used for identifying the particle diameters of small crystal grains. The average equivalent circle diameter was calculated from the observation results. In addition, the relative density was evaluated through use of the theoretical density calculated from the lattice constant obtained from X-ray diffraction and the weighed composition, and the measured density by the Archimedes method.

Next, the obtained disc-shaped sintered compact was abraded on both surfaces through use of an abrasive machine while the size of abrasive grains was changed so that the thickness became 0.5 mm, and finally, finishing abrasion was performed through use of the abrasive machine with abrasive grains of #2,000.

Then, the surface roughness Ra was measured on each of the abraded surfaces of the sintered compact. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 μm, and a sampling rate of 200 Sa per second. As a result, the surface roughness Ra was 0.19 μm.

Next, the crystal structure of the abraded sintered compact was analyzed by X-ray diffraction. As a result, only peaks corresponding to a perovskite structure were observed.

Next, the composition of the sintered compact obtained by the ICP emission spectrochemical analysis was evaluated. As a result, the composition of Ba, Ca, Ti, and Mn after the sintering was matched with the weighed composition.

Next, the abraded sintered compact was placed in an electric furnace and held in the air at a maximum temperature of 990° C. for 120 minutes for annealing, to thereby obtain the piezoelectric ceramics of the present disclosure. Then, the surface roughness Ra was measured on each of the abraded surfaces of the obtained piezoelectric ceramics. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 μm, and a sampling rate of 200 Sa per second. As a result, the surface roughness Ra after the annealing was 0.19 μm, which was the same as the surface roughness Ra before the annealing.

Next, gold electrodes each having a thickness of 400 nm were formed on the front and rear surfaces of the piezoelectric ceramics by DC sputtering. Titanium was formed into a film having a thickness of 30 nm as a contact layer between the electrodes and the ceramics. The ceramics with the electrodes was cut to produce a strip-shaped piezoelectric element of the present disclosure having a size of 10 mm×2.5 mm×0.5 mm. The surface of a hot plate was set to from 60° C. to 100° C., and an electric field of 1 kV/mm was applied to the obtained piezoelectric element on the hot plate for 30 minutes. Thus, polarization treatment was performed.

Subsequently, through the same steps as those in Example 1, the crystal structure of the piezoelectric ceramics forming the piezoelectric element of the present disclosure, the surface roughness Ra before and after the annealing, the electromechanical coupling coefficient $k_{31}$, and the fluctuation rate of $k_{31}$ within each temperature range, the mechanical quality factor Qm, and the power consumption were evaluated. The results are shown in Table 2.

Example 13

As raw material powders, barium titanate (BaTiO$_3$, Ba/Ti=0.9985) having an average particle diameter of 100 nm, calcium titanate (CaTiO$_3$, Ca/Ti=0.9978), calcium zirconate (CaZrO$_3$, Ca/Zr=0.999), trimanganese tetraoxide (Mn$_3$O$_4$), and barium carbonate for adjusting a ratio "a" of a sum of the numbers of moles of Ti and Zr to a sum of the numbers of moles of Ba and Ca were used.

Those raw material powders were weighed so as to obtain a ratio of the composition formula (Ba$_{0.86}$,Ca$_{0.14}$)$_{1.0026}$(Ti$_{0.94}$,Zr$_{0.06}$)O$_3$ containing titanium and barium as main components. Mn was added to 100 parts by weight of this metal oxide so that the content of Mn became 0.10 part by weight in terms of a metal. Further, the metal oxide having Mn added thereto was mixed by dry mixing for 24 hours through use of a ball mill. In order to granulate the obtained mixed powder, 3 parts by weight of a PVA binder based on the mixed powder was caused to adhere to the surface of the mixed powder through use of a spray dryer device.

Next, the obtained granulated powder was filled in a mold, and a molding pressure of 200 MPa was applied thereto using a press molding machine to produce a disc-shaped compact. The compact may be further pressurized using a cold isostatic pressing molding machine.

The obtained compact was placed in an electric furnace, kept at a maximum temperature of 1,340° C. for 5 hours, and sintered in an air atmosphere over a total of 24 hours to provide a sintered compact.

Then, the average equivalent circle diameter and the relative density of crystal grains forming the obtained sintered compact were evaluated. As a result, the average equivalent circle diameter was 10 and the relative density was 96%. A polarizing microscope was mainly used for observing the crystal grains. A scanning electron microscope (SEM) was used for identifying the particle diameters of small crystal grains. The average equivalent circle diameter was calculated from the observation results. In addition, the relative density was evaluated through use of the theoretical density calculated from the lattice constant obtained from X-ray diffraction and the weighed composition, and the measured density by the Archimedes method.

Next, the obtained disc-shaped sintered compact was abraded on both surfaces through use of an abrasive machine while the size of abrasive grains was changed so that the thickness became 0.5 mm, and finally, finishing abrasion was performed through use of the abrasive machine with abrasive grains of #2,000.

Then, the surface roughness Ra was measured on each of the abraded surfaces of the sintered compact. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 and a sampling rate of 200 Sa per second. As a result, the surface roughness Ra was 0.19 μm.

Next, the crystal structure of the abraded sintered compact was analyzed by X-ray diffraction. As a result, only peaks corresponding to a perovskite structure were observed.

Next, the composition of the sintered compact obtained by the ICP emission spectrochemical analysis was evaluated. As a result, the composition of Ba, Ca, Ti, Zr, and Mn after the sintering was matched with the weighed composition.

Next, the abraded sintered compact was placed in an electric furnace and held in the air at a maximum temperature of 990° C. for 120 minutes for annealing, to thereby obtain the piezoelectric ceramics of the present disclosure. Then, the surface roughness Ra was measured on each of the abraded surfaces of the obtained piezoelectric ceramics. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 and a sampling rate of 200 Sa per second. As a result, the surface roughness Ra after the annealing was 0.19 which was the same as the surface roughness Ra before the annealing.

Next, gold electrodes each having a thickness of 400 nm were formed on the front and rear surfaces of the piezoelectric ceramics by DC sputtering. Titanium was formed into a film having a thickness of 30 nm as a contact layer between the electrodes and the ceramics. The ceramics with the electrodes was cut to produce a strip-shaped piezoelectric element of the present disclosure having a size of 10 mm×2.5 mm×0.5 mm. The surface of a hot plate was set to from 60° C. to 100° C., and an electric field of 1 kV/mm was applied to the obtained piezoelectric element on the hot plate for 30 minutes. Thus, polarization treatment was performed.

Subsequently, through the same steps as those in Example 1, the crystal structure of the piezoelectric ceramics forming the piezoelectric element of the present disclosure, the surface roughness Ra before and after the annealing, the electromechanical coupling coefficient k$_{31}$, and the fluctuation rate of k$_{31}$ within each temperature range, the mechanical quality factor Qm, and the power consumption were evaluated. The results are shown in Table 2.

Comparative Example 1

As raw material powders, barium titanate (BaTiO$_3$, Ba/Ti=0.9985) having an average particle diameter of 100 nm, calcium titanate (CaTiO$_3$, Ca/Ti=0.9978), calcium zirconate (CaZrO$_3$, Ca/Zr=0.999), bismuth oxide (Bi$_2$O$_3$), trimanganese tetraoxide (Mn$_3$O$_4$), and barium carbonate for adjusting a ratio "a" of a sum of the numbers of moles of Ti and Zr to a sum of the numbers of moles of Ba and Ca were used. Those raw material powders were weighed so as to obtain a ratio of the composition formula (Ba$_{0.86}$,Ca$_{0.14}$)$_{1.002}$(Ti$_{0.93}$,Zr$_{0.07}$)O$_3$ containing titanium and barium as main components. Mn was added to 100 parts by weight of this metal oxide so that the content of Mn became 0.16 part by weight in terms of a metal. Further, Bi was added to the metal oxide having Mn added thereto so that the content of Bi became 0.17 part by weight in terms of a metal, and the resultant was mixed by dry mixing for 24 hours through use of a ball mill. In order to granulate the obtained mixed powder, 3 parts by weight of a PVA binder based on the mixed powder was caused to adhere to the surface of the mixed powder through use of a spray dryer device.

Next, the obtained granulated powder was filled in a mold, and a forming pressure of 200 MPa was applied thereto using a press molding machine to produce a disc-shaped compact. The compact may be further pressurized using a cold isostatic pressing molding machine.

The obtained compact was placed in an electric furnace, kept at a maximum temperature of 1,300° C. for 5 hours, and sintered in an air atmosphere over a total of 24 hours to provide a sintered compact.

Then, the average equivalent circle diameter and the relative density of crystal grains forming the obtained sintered compact were evaluated. As a result, the average equivalent circle diameter was 7 and the relative density was 96%. A polarizing microscope was mainly used for observing the crystal grains. A scanning electron microscope (SEM) was used for identifying the particle diameters of small crystal grains. The average equivalent circle diameter was calculated from the observation results. In addition, the relative density was evaluated through use of the theoretical density calculated from the lattice constant obtained from X-ray diffraction and the weighed composition, and the measured density by the Archimedes method.

Next, the obtained disc-shaped sintered compact was abraded on both surfaces through use of an abrasive machine while the size of abrasive grains was changed so that the thickness became 0.5 mm, and finally, finishing abrasion was performed through use of the abrasive machine with abrasive grains of #2,000, to thereby obtain a piezoelectric ceramics of Comparative Example 1.

Then, the surface roughness Ra was measured on each of the abraded surfaces of the piezoelectric ceramics. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 μm, and a sampling rate of 200 Sa per second. As a result, the surface roughness Ra was 0.13 μm.

Next, the crystal structure of the abraded sintered compact was analyzed by X-ray diffraction. As a result, only peaks corresponding to a perovskite structure were observed.

Next, the composition of the sintered compact obtained by the ICP emission spectrochemical analysis was evaluated. As a result, the composition of Ba, Ca, Ti, Zr, Mn, and Bi after the sintering was matched with the weighed composition.

Next, gold electrodes each having a thickness of 400 nm were formed on the front and rear surfaces of the piezoelectric ceramics by DC sputtering. Titanium was formed into a film having a thickness of 30 nm as a contact layer between the electrodes and the ceramics. The ceramics with the electrodes was cut to produce a strip-shaped piezoelectric element of Comparative Example 1 having a size of 10 mm×2.5 mm×0.5 mm. The surface of a hot plate was set to from 60° C. to 100° C., and an electric field of 1 kV/mm was applied to the obtained piezoelectric element on the hot plate for 30 minutes. Thus, polarization treatment was performed.

Subsequently, through the same steps as those in Example 1, the crystal structure of the piezoelectric ceramics of Comparative Example 1 forming the piezoelectric element, the surface roughness Ra after the abrading step, the electromechanical coupling coefficient $k_{31}$, and the fluctuation rate of $k_{31}$ within each temperature range, the mechanical quality factor Qm, and the power consumption were evaluated. The results are shown in Table 2.

Comparative Example 2

A piezoelectric ceramics and a piezoelectric element of Comparative Example 2 were obtained through the same steps as those in Comparative Example 1 except that the annealing step was performed after the abrading step.

After the abrading step, the abraded sintered compact was placed in an electric furnace and held in the air at a maximum temperature of 1,000° C. for 600 minutes for annealing, to thereby obtain the piezoelectric ceramics of Comparative Example 2. Then, the surface roughness Ra was measured on each of the abraded surfaces of the obtained piezoelectric ceramics. The measurement of the roughness Ra was performed through use of a stylus type surface profilometer with a stylus having a radius of curvature of 1 μm at a distal end portion thereof. The measurement conditions for the surface roughness Ra were a stylus scanning speed of 5 μm per second, a scanning distance of 200 μm, and a sampling rate of 200 Sa per second. As a result, the surface roughness Ra after the annealing was 0.20 μm, which was a value larger than the surface roughness Ra before the annealing. In Comparative Example 2, it is conceived that the annealing was performed at 1,000° C., and hence crystal grains grew on the abraded surface to increase the surface roughness Ra.

In the abrading step, both surfaces were abraded through use of an abrasive machine while the size of abrasive grains was changed so that the thickness became 0.5 mm, and finally, finishing abrasion was performed through use of the abrasive machine with abrasive grains of No. 4,000. Specific numerical numbers of the maximum temperature and the retention time of the maximum temperature in the annealing step are shown in Table 1.

Subsequently, through the same steps as those in Example 1, the crystal structure of the piezoelectric ceramics forming the piezoelectric element of the present disclosure, the surface roughness Ra before and after the annealing, the electromechanical coupling coefficient $k_{31}$, and the fluctuation rate of $k_{31}$ within each temperature range, the mechanical quality factor Qm, and the power consumption were evaluated. The results are shown in Table 2.

TABLE 1

| | Composition of piezoelectric ceramics | Sintering temperature (° C.) | Annealing temperature (° C.) | Retention time (min) | Electrode type | Electrode baking temperature (° C.) | Retention time of electrode baking temperature (min) |
|---|---|---|---|---|---|---|---|
| Example 1 | $(Ba_{0.86}Ca_{0.14})_{1.002}(Ti_{0.93}Zr_{0.07})O_3$ + Mn0.16 wt % + Bi0.17 wt % | 1,300 | 990 | 120 | Au | — | — |
| Example 2 | $(Ba_{0.86}Ca_{0.14})_{1.002}(Ti_{0.93}Zr_{0.07})O_3$ + Mn0.16 wt % + Bi0.17 wt % | 1,300 | 800 | 6 | Au | — | — |
| Example 3 | $(Ba_{0.86}Ca_{0.14})_{1.002}(Ti_{0.93}Zr_{0.07})O_3$ + Mn0.16 wt % + Bi0.17 wt % | 1,300 | 900 | 6 | Au | — | — |
| Example 4 | $(Ba_{0.86}Ca_{0.14})_{1.002}(Ti_{0.93}Zr_{0.07})O_3$ + Mn0.16 wt % + Bi0.17 wt % | 1,300 | 950 | 6 | Au | — | — |
| Example 5 | $(Ba_{0.86}Ca_{0.14})_{1.002}(Ti_{0.93}Zr_{0.07})O_3$ + Mn0.16 wt % + Bi0.17 wt % | 1,300 | 990 | 6 | Au | — | — |
| Example 6 | $(Ba_{0.86}Ca_{0.14})_{1.002}(Ti_{0.93}Zr_{0.07})O_3$ + Mn0.16 wt % + Bi0.17 wt % | 1,300 | 950 | 480 | Au | — | — |
| Example 7 | $(Ba_{0.86}Ca_{0.14})_{1.002}(Ti_{0.93}Zr_{0.07})O_3$ + Mn0.16 wt % + Bi0.17 wt % | 1,300 | 950 | 120 | Au | — | — |

TABLE 1-continued

| | Composition of piezoelectric ceramics | Sintering temperature (° C.) | Annealing temperature (° C.) | Retention time (min) | Electrode type | Electrode baking temperature (° C.) | Retention time of electrode baking temperature (min) |
|---|---|---|---|---|---|---|---|
| Example 8 | $(Ba_{0.86}Ca_{0.14})_{1.002}(Ti_{0.93}Zr_{0.07})O_3$ + Mn0.16 wt % + Bi0.17 wt % | 1,300 | 950 | 290 | Au | — | — |
| Example 9 | $(Ba_{0.86}Ca_{0.14})_{1.002}(Ti_{0.93}Zr_{0.07})O_3$ + Mn0.16 wt % + Bi0.17 wt % | 1,300 | — | — | Ag | 800 | 10 |
| Example 10 | $(Ba_{0.86}Ca_{0.14})_{1.002}(Ti_{0.93}Zr_{0.07})O_3$ + Mn0.16 wt % + Bi0.17 wt % | 1,300 | — | — | Ag | 990 | 10 |
| Example 11 | $(Ba_{0.86}Ca_{0.14})_{1.002}(Ti_{0.93}Zr_{0.07})O_3$ + Mn0.16 wt % + Bi0.17 wt % | 1,300 | 950 | 120 | Ag | 900 | 10 |
| Example 12 | $(Ba_{0.96}Ca_{0.04})_{1.005}TiO_3$ + Mn0.1 wt % | 1,200 | 990 | 120 | Au | — | — |
| Example 13 | $(Ba_{0.86}Ca_{0.14})_{0.989}(Ti_{0.93}Zr_{0.07})O_3$ + Mn0.14 wt % | 1,340 | 990 | 120 | Au | — | — |
| Comparative Example 1 | $(Ba_{0.86}Ca_{0.14})_{1.002}(Ti_{0.93}Zr_{0.07})O_3$ + Mn0.16 wt % + Bi0.17 wt % | 1,300 | No annealing | No annealing | Au | — | — |
| Comparative Example 2 | $(Ba_{0.86}Ca_{0.14})_{1.002}(Ti_{0.93}Zr_{0.07})O_3$ + Mn0.16 wt % + Bi0.17 wt % | 1,300 | 1,000 | 600 | Au | — | — |

TABLE 2

| | Electromechanical coupling coefficient $k_{31}$ (—) | Ra after abrading step (μm) | Ra after annealing step (μm) | Fluctuation rate of $k_{31}$ at 0° C. or more and 60° C. or less (%) | Mechanical quality factor Qm (—) | Average equivalent circle diameter (μm) | Relative density (%) | Power consumption (mW) |
|---|---|---|---|---|---|---|---|---|
| Example 1 | 0.281 | 0.03 | 0.03 | 24 | 1,250 | 8 | 98 | 15 |
| Example 2 | 0.255 | 0.13 | 0.13 | 26 | 1,263 | 7 | 96 | 26 |
| Example 3 | 0.257 | 0.13 | 0.13 | 24 | 1,244 | 7 | 97 | 24 |
| Example 4 | 0.261 | 0.14 | 0.14 | 24 | 1,250 | 7 | 97 | 22 |
| Example 5 | 0.265 | 0.13 | 0.14 | 25 | 1,255 | 8 | 97 | 20 |
| Example 6 | 0.264 | 0.13 | 0.13 | 25 | 1,249 | 7 | 97 | 20 |
| Example 7 | 0.275 | 0.13 | 0.15 | 24 | 1,266 | 7 | 97 | 15 |
| Example 8 | 0.275 | 0.14 | 0.14 | 24 | 1,267 | 7 | 97 | 15 |
| Example 9 | 0.255 | 0.13 | 0.13 | 25 | 1,261 | 7 | 97 | 25 |
| Example 10 | 0.260 | 0.13 | 0.13 | 25 | 1,260 | 7 | 97 | 21 |
| Example 11 | 0.275 | 0.13 | 0.13 | 26 | 1,280 | 8 | 97 | 16 |
| Example 12 | 0.252 | 0.19 | 0.19 | 29 | 1,050 | 10 | 96 | 27 |
| Example 13 | 0.252 | 0.19 | 0.19 | 25 | 1,090 | 10 | 96 | 28 |
| Comparative Example 1 | 0.240 | 0.13 | — | 28 | 1,215 | 7 | 96 | 35 |
| Comparative Example 2 | 0.250 | 0.13 | 0.20 | 30 | 1,230 | 8 | 97 | 31 |

Example 14

An ultrasonic motor illustrated in FIG. 2 was produced through use of the piezoelectric element of Example 1. In the produced ultrasonic motor, the rotation of the motor in accordance with the application of an AC voltage was recognized.

Example 15

An optical apparatus illustrated in FIG. 3A and FIG. 3B was produced through use of the ultrasonic motor of Example 14. In the produced optical apparatus, an autofocus operation in accordance with the application of an AC voltage was recognized.

Example 16

A dust removing device illustrated in FIG. 5A and FIG. 5B was produced through use of the piezoelectric element of Example 1. In the produced dust removing device, when plastic beads were sprayed and an AC voltage was applied, a satisfactory dust removing rate was recognized.

Example 17

An image pickup apparatus illustrated in FIG. 8 was produced through use of the dust removing device of Example 16. When the produced image pickup apparatus was operated, dust on the surface of an image pickup unit was satisfactorily removed, and an image without dust defects was obtained.

Example 18

An ultrasonic probe illustrated in FIG. 10 was produced through use of the piezoelectric element of Example 1. In the produced ultrasonic probe, ultrasonic waves were transmitted by the application of an AC voltage, and a reception signal caused by reflection from the inside of an object was recognized.

Example 19

An ultrasonic diagnostic apparatus illustrated in FIG. 11 was produced through use of the ultrasonic probe of Example 18. When the produced ultrasonic diagnostic apparatus was operated, an image of the inside of an object was clearly output.

Example 20

An electronic apparatus illustrated in FIG. 12 was produced through use of the piezoelectric element of Example 1. In the produced electronic apparatus, a speaker operation in accordance with the application of an AC voltage was recognized.

The piezoelectric ceramics of the present disclosure has a large electromechanical coupling coefficient, and hence has high piezoelectricity. In addition, the piezoelectric ceramics does not contain lead, and hence has a less burden on the environment. Thus, the piezoelectric ceramics of the present disclosure can be used without problems also in a large number of devices, such as an ultrasonic motor, a dust removing device, and an ultrasonic probe which use the piezoelectric ceramics.

According to the present disclosure, the piezoelectric ceramics which does not contain lead, has small temperature dependence of the electromechanical coupling coefficient within the operating temperature range of the piezoelectric element, and has a high density, a high mechanical quality factor, satisfactory piezoelectric characteristics, and a small surface roughness can be provided. The piezoelectric ceramics of the present disclosure does not use lead, and hence has a small burden on the environment.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-074641, filed Apr. 20, 2020, which is hereby incorporated by reference herein in its entirety.

What is claimed is:

1. A piezoelectric ceramics comprising titanium and barium as main components,
   wherein the piezoelectric ceramics has an electromechanical coupling coefficient $k_{31}$ at room temperature of 0.252 or more, and
   wherein the piezoelectric ceramics has a roughness Ra of 0.19 μm or less on at least a part of a surface thereof.

2. The piezoelectric ceramics according to claim 1,
   wherein the piezoelectric ceramics contains an oxide containing Ba, Ca, Ti, and Zr, and Mn,
   wherein a molar ratio "x" of the Ca with respect to a sum of the Ba and the Ca is 0.02≤x≤0.30,
   wherein a molar ratio "y" of the Zr with respect to a sum of the Ti and the Zr is 0.020≤y≤0.095,
   wherein the molar ratio "y" and the molar ratio "x" has a relationship of y≤x,
   wherein a molar ratio "a" of the sum of the Ba and the Ca with respect to the sum of the Ti and the Zr is 1.00≤a≤1.01, and
   wherein a content of the Mn with respect to 100 parts by weight of the oxide is 0.02 part by weight or more and 0.40 part by weight or less in terms of a metal.

3. The piezoelectric ceramics according to claim 1, wherein a fluctuation rate of the electromechanical coupling coefficient $k_{31}$ is 35% or less within a temperature range of 0° C. to 60° C.

4. The piezoelectric ceramics according to claim 1, wherein the piezoelectric ceramics has a mechanical quality factor Qm of 1,000 or more.

5. The piezoelectric ceramics according to claim 1, wherein the piezoelectric ceramics is formed of crystal grains having an average equivalent circle diameter of 1 μm to 10 μm.

6. The piezoelectric ceramics according to claim 1, wherein the piezoelectric ceramics has a relative density of 93% to 100%.

7. A piezoelectric element comprising:
   an electrode; and
   a piezoelectric ceramics,
   wherein the piezoelectric ceramics is the piezoelectric ceramics of claim 1.

8. An ultrasonic motor comprising:
   a vibrating body in which the piezoelectric element of claim 7 is arranged; and
   a contact body configured to be brought into contact with the vibrating body to move relative to the vibrating body.

9. An optical apparatus comprising:
   a drive unit; and
   the ultrasonic motor of claim 8 provided to the drive unit.

10. A vibration device comprising a vibrating body in which the piezoelectric element of claim 7 is arranged on a vibrating plate.

11. A dust removing device comprising:
    a vibrating portion; and
    the vibration device of claim 10 provided to the vibrating portion.

12. An image pickup apparatus comprising:
    the dust removing device of claim 11; and
    an image pickup element unit,
    wherein a vibrating plate of the dust removing device is arranged on a light receiving surface side of the image pickup element unit.

13. An ultrasonic probe comprising:
    a housing; and
    the piezoelectric element of claim 7 configured to transmit and receive a signal.

14. An ultrasonic diagnostic apparatus comprising:
    the ultrasonic probe of claim 13;
    an image processing unit configured to process an obtained signal; and
    an image display portion configured to display image data processed by the image processing unit.

15. The ultrasonic diagnostic apparatus according to claim 14, further comprising a cable configured to connect the ultrasonic probe and the image processing unit in a communicable manner.

16. A piezoelectric acoustic component comprising the piezoelectric element of claim 7.

17. An electronic apparatus comprising:
    a member; and
    the piezoelectric element of claim 7 arranged on the member.

* * * * *